US012319712B2

(12) United States Patent
Rajasekaran et al.

(10) Patent No.: US 12,319,712 B2
(45) Date of Patent: Jun. 3, 2025

(54) METHODS OF SYNTHESIZING A POLYNUCLEOTIDE ARRAY USING PHOTOACTIVATED AGENTS

(71) Applicant: Vibrant Holdings, LLC, San Carlos, CA (US)

(72) Inventors: John J. Rajasekaran, Hillsborough, CA (US); Vasanth Jayaraman, San Mateo, CA (US); Anirudh Venugopal, San Mateo, CA (US); Kang Bei, San Mateo, CA (US); Tianhao Wang, San Mateo, CA (US); Karthik Krishna, Hillsborough, CA (US); Hari Krishnan Krishnamurthy, San Mateo, CA (US)

(73) Assignee: Vibrant Holdings, LLC, Santa Clara, CA (US)

( * ) Notice: Subject to any disclaimer, the term of this patent is extended or adjusted under 35 U.S.C. 154(b) by 1000 days.

(21) Appl. No.: 17/054,067

(22) PCT Filed: May 9, 2019

(86) PCT No.: PCT/US2019/031555
§ 371 (c)(1),
(2) Date: Nov. 9, 2020

(87) PCT Pub. No.: WO2019/217704
PCT Pub. Date: Nov. 14, 2019

(65) Prior Publication Data
US 2021/0380629 A1 Dec. 9, 2021

Related U.S. Application Data

(60) Provisional application No. 62/668,964, filed on May 9, 2018.

(51) Int. Cl.
C12Q 1/6806 (2018.01)
C07H 21/04 (2006.01)
G03F 7/004 (2006.01)
G03F 7/20 (2006.01)

(52) U.S. Cl.
CPC ............ *C07H 21/04* (2013.01); *G03F 7/0045* (2013.01); *G03F 7/2004* (2013.01); *C07B 2200/11* (2013.01); *C12Q 1/6806* (2013.01)

(58) Field of Classification Search
CPC .... B01J 19/0046; G03F 7/2004; G03F 7/0045
See application file for complete search history.

(56) References Cited

U.S. PATENT DOCUMENTS

| | | |
|---|---|---|
| 4,780,405 A | 10/1988 | Kaiser et al. |
| 5,069,996 A | 12/1991 | Rogler |
| 5,143,854 A | 9/1992 | Pirrung et al. |
| 5,240,811 A | 8/1993 | Taylor et al. |
| 5,310,687 A | 5/1994 | Bard et al. |
| 5,866,434 A | 2/1999 | Massey et al. |
| 5,919,523 A | 7/1999 | Sundberg et al. |
| 5,945,286 A | 8/1999 | Krihak et al. |
| 6,017,696 A | 1/2000 | Heller |
| 6,040,138 A | 3/2000 | Lockhart et al. |
| 6,083,697 A | 7/2000 | Beecher et al. |
| 6,140,045 A | 10/2000 | Wohlstadter et al. |
| 6,316,230 B1 | 11/2001 | Egholm et al. |
| 6,319,726 B1 | 11/2001 | Schuppan et al. |
| 6,359,125 B1 | 3/2002 | Kim et al. |
| 6,395,474 B1 | 5/2002 | Buchardt et al. |
| 6,469,151 B1 | 10/2002 | Egholm et al. |
| 6,506,558 B1 | 1/2003 | Fodor et al. |
| 6,521,181 B1 | 2/2003 | Northrup et al. |
| 6,861,216 B2 | 3/2005 | Neriishi et al. |
| 6,943,034 B1 | 9/2005 | Winkler et al. |
| 6,969,766 B2 | 11/2005 | Kim et al. |
| 7,022,851 B2 | 4/2006 | Kim et al. |
| 7,041,453 B2 | 5/2006 | Yang |
| 7,125,994 B2 | 10/2006 | Kim et al. |
| 7,145,006 B2 | 12/2006 | Kim et al. |
| 7,179,896 B2 | 2/2007 | Kim et al. |
| 7,211,668 B2 | 5/2007 | Kim et al. |
| 7,320,864 B2 | 1/2008 | Yang |
| 7,476,504 B2 | 1/2009 | Turner |
| 7,510,841 B2 | 3/2009 | Stuelpnagel et al. |
| 7,527,912 B2 | 5/2009 | Ohsawa et al. |
| 7,544,638 B2 | 6/2009 | Gao et al. |
| 7,553,943 B2 | 6/2009 | Ellis et al. |
| 7,608,397 B2 | 10/2009 | Densham |

(Continued)

FOREIGN PATENT DOCUMENTS

| | | |
|---|---|---|
| CN | 103234948 | 8/2013 |
| CN | 103675291 A | 3/2014 |

(Continued)

OTHER PUBLICATIONS

US 6,200,755 B1, 08/2006, Gordon et al. (withdrawn)

(Continued)

*Primary Examiner* — Bahar Craigo

(74) *Attorney, Agent, or Firm* — Goodwin Procter LLP

(57) ABSTRACT

Described herein are methods for the synthesis of DNA polynucleotides and polynucleotides, as well as methods for their deprotection and methods for the use of said compounds and compositions comprising said compounds. In particular, such compounds and compositions comprising them are used in methods for light-directed synthesis of DNA microarrays.

13 Claims, 5 Drawing Sheets
Specification includes a Sequence Listing.

(56) References Cited

U.S. PATENT DOCUMENTS

| | | |
|---|---|---|
| 7,622,279 B2 | 11/2009 | Ju |
| 7,659,064 B2 | 2/2010 | Park et al. |
| 7,862,996 B2 | 1/2011 | Kuimelis et al. |
| 7,956,011 B2 * | 6/2011 | Serafinowski ....... B01J 19/0046 506/13 |
| 8,128,908 B2 | 3/2012 | Santra et al. |
| 8,133,985 B2 | 3/2012 | Lee et al. |
| 8,252,533 B2 | 8/2012 | Park et al. |
| 8,546,437 B2 | 10/2013 | Quart et al. |
| 8,969,002 B2 | 3/2015 | Esfandyarpour et al. |
| 9,216,399 B2 | 12/2015 | Rajasekaran et al. |
| 9,417,236 B2 | 8/2016 | Rajasekaran et al. |
| 9,631,231 B2 | 4/2017 | Shaffer et al. |
| 9,766,200 B2 | 9/2017 | Toumazou et al. |
| 10,006,909 B2 | 6/2018 | Rajasekaran et al. |
| 10,040,818 B2 | 8/2018 | Jayaraman |
| 10,316,363 B2 | 6/2019 | Ansari et al. |
| 10,538,808 B2 | 1/2020 | Rajasekaran |
| 2002/0076834 A1 | 6/2002 | Detlef et al. |
| 2002/0086319 A1 | 7/2002 | Ellson et al. |
| 2003/0068446 A1 | 4/2003 | Mirkin et al. |
| 2003/0082294 A1 | 5/2003 | Bruhn et al. |
| 2003/0124029 A1 | 7/2003 | Webb et al. |
| 2003/0148401 A1 | 8/2003 | Agrawal et al. |
| 2003/0228605 A1 | 12/2003 | Slootstra et al. |
| 2004/0027093 A1 | 2/2004 | Tashiro et al. |
| 2004/0038388 A1 | 2/2004 | Yamamoto et al. |
| 2004/0110133 A1 | 6/2004 | Xu et al. |
| 2005/0221351 A1 | 10/2005 | Ryu |
| 2005/0240811 A1 | 10/2005 | Safford et al. |
| 2005/0244863 A1 | 11/2005 | Mir |
| 2005/0260611 A1 | 11/2005 | Wang et al. |
| 2006/0088863 A1 | 4/2006 | Yamamoto et al. |
| 2006/0147949 A1 | 7/2006 | Ha et al. |
| 2006/0172340 A1 | 8/2006 | Wohlstadter et al. |
| 2007/0122841 A1 | 5/2007 | Rajasekaran et al. |
| 2007/0122842 A1 | 5/2007 | Rajasekaran et al. |
| 2007/0154946 A1 | 7/2007 | Rajasekaran et al. |
| 2007/0161778 A1 | 7/2007 | Kuimelis et al. |
| 2007/0231794 A1 | 10/2007 | Dill et al. |
| 2008/0108149 A1 | 5/2008 | Sundararajan et al. |
| 2009/0311727 A1 | 12/2009 | Watkins et al. |
| 2009/0325816 A1 | 12/2009 | Mirkin et al. |
| 2010/0028559 A1 | 2/2010 | Yan et al. |
| 2010/0093554 A1 | 4/2010 | Chu |
| 2010/0120630 A1 | 5/2010 | Huang et al. |
| 2010/0222547 A1 | 9/2010 | Rajagopalan et al. |
| 2010/0240555 A1 | 9/2010 | Sundararajan et al. |
| 2010/0245057 A1 | 9/2010 | Chamarti et al. |
| 2010/0304303 A1 | 12/2010 | Maeda et al. |
| 2011/0097762 A1 | 4/2011 | Gao et al. |
| 2011/0190210 A1 | 8/2011 | Adini et al. |
| 2011/0281766 A1 | 11/2011 | Cooper |
| 2011/0293644 A1 | 12/2011 | Anderson et al. |
| 2011/0303027 A1 | 12/2011 | Shirazi et al. |
| 2012/0172309 A1 | 7/2012 | Dal Farra et al. |
| 2012/0183981 A1 | 7/2012 | Norman et al. |
| 2012/0238477 A1 | 9/2012 | Albert et al. |
| 2012/0245057 A1 | 9/2012 | Albert et al. |
| 2013/0084532 A1 | 4/2013 | Wu et al. |
| 2014/0031239 A1 | 1/2014 | Kotsbak |
| 2014/0072963 A1 | 3/2014 | Qin |
| 2014/0073511 A1 | 3/2014 | Wong et al. |
| 2014/0349888 A1 | 11/2014 | Rajasekaran et al. |
| 2015/0038373 A1 | 2/2015 | Banyai et al. |
| 2015/0246336 A1 | 9/2015 | Somoza et al. |
| 2016/0009737 A1 | 1/2016 | Ikeda et al. |
| 2016/0144368 A1 | 5/2016 | Isami et al. |
| 2016/0186252 A1 | 6/2016 | Esfandyarpour et al. |
| 2016/0193608 A1 | 7/2016 | Isami et al. |
| 2017/0168047 A1 | 6/2017 | Aghvanyan et al. |
| 2017/0192007 A1 | 7/2017 | Rajasekaran et al. |
| 2018/0106795 A1 | 4/2018 | Rajasekaran et al. |
| 2018/0218250 A1 | 8/2018 | David et al. |
| 2019/0194745 A1 | 6/2019 | Rajasekaran |
| 2019/0217704 A1 | 7/2019 | Tschanz |
| 2019/0262794 A1 | 8/2019 | Rajasekaran |
| 2019/0366291 A1 | 12/2019 | Rajasekaran et al. |
| 2020/0095635 A1 | 3/2020 | Rajasekaran |
| 2022/0162698 A1 | 5/2022 | Rajasekaran |

FOREIGN PATENT DOCUMENTS

| | | |
|---|---|---|
| EP | 1077264 A2 | 2/2001 |
| EP | 1517178 A1 | 3/2005 |
| EP | 0854937 B1 | 5/2005 |
| EP | 1198594 B1 | 5/2005 |
| EP | 1470114 B1 | 8/2009 |
| EP | 1651642 B1 | 11/2009 |
| EP | 1501812 B1 | 12/2009 |
| EP | 2174936 A1 | 4/2010 |
| EP | 1025120 B1 | 8/2010 |
| EP | 2003501 B1 | 10/2010 |
| EP | 2094863 B1 | 8/2014 |
| EP | 3790985 A1 | 3/2021 |
| JP | H05294995 A | 11/1993 |
| JP | H06500308 A | 1/1994 |
| JP | 2001503856 A | 3/2001 |
| JP | 2002500362 A | 1/2002 |
| JP | 2002502698 A | 1/2002 |
| JP | 2002520618 A | 7/2002 |
| JP | 2002525577 A | 8/2002 |
| JP | 2003517149 A | 5/2003 |
| JP | 2003523348 A | 8/2003 |
| JP | 2003524193 A | 8/2003 |
| JP | 2003342354 A | 12/2003 |
| JP | 2006519285 | 9/2004 |
| JP | 2004534226 A | 11/2004 |
| JP | 2005512032 A | 4/2005 |
| JP | 2005513999 A | 5/2005 |
| JP | 2005521032 A | 7/2005 |
| JP | 2005264156 A | 9/2005 |
| JP | 2005530983 A | 10/2005 |
| JP | 2006512893 A | 4/2006 |
| JP | 2006275152 A1 | 10/2006 |
| JP | 2007504462 A | 3/2007 |
| JP | 2008157952 A | 7/2008 |
| JP | 2008170449 A | 7/2008 |
| JP | 2009510786 A | 3/2009 |
| JP | 2009075131 A | 4/2009 |
| JP | 2009534200 A | 9/2009 |
| JP | 2010507099 A | 3/2010 |
| JP | 2010215816 A | 9/2010 |
| JP | 2011013118 A | 1/2011 |
| JP | 2011017711 A | 1/2011 |
| JP | 2011519168 A | 6/2011 |
| JP | 2011234723 A | 11/2011 |
| JP | 2012510431 A | 5/2012 |
| JP | 2012163491 A | 8/2012 |
| JP | 2012518294 A | 8/2012 |
| WO | 1994/28075 A1 | 12/1994 |
| WO | 98/03872 A2 | 1/1998 |
| WO | 98/12539 A1 | 3/1998 |
| WO | 1999/41007 A2 | 8/1999 |
| WO | 2000/16089 A2 | 3/2000 |
| WO | 2001/43870 A2 | 6/2001 |
| WO | 2003/001889 A2 | 1/2003 |
| WO | 2003/023360 A2 | 3/2003 |
| WO | 2003/038033 A2 | 5/2003 |
| WO | 2003/104273 A2 | 12/2003 |
| WO | 2004/027093 A1 | 4/2004 |
| WO | 2005/014696 A1 | 2/2005 |
| WO | 2007/038647 A2 | 4/2007 |
| WO | 2007/078868 A1 | 7/2007 |
| WO | 2008/097370 A2 | 8/2008 |
| WO | 2008/118167 A1 | 10/2008 |
| WO | 2008/151146 A2 | 12/2008 |
| WO | 2009/132321 A1 | 10/2009 |
| WO | 2010/060155 A1 | 6/2010 |
| WO | 2010/085763 A1 | 7/2010 |
| WO | 2010/096593 A2 | 8/2010 |
| WO | 2011/027048 A1 | 3/2011 |
| WO | 2011/034620 A2 | 3/2011 |
| WO | 2011/058136 A1 | 5/2011 |

(56) References Cited

FOREIGN PATENT DOCUMENTS

| WO | 2012/122929 A1 | 9/2012 |
|---|---|---|
| WO | 2012/122959 A1 | 9/2012 |
| WO | 2012/154594 A1 | 11/2012 |
| WO | 2012/174479 A1 | 12/2012 |
| WO | 2013/119845 A1 | 8/2013 |
| WO | 2014/052989 A2 | 4/2014 |
| WO | 2014/078606 A2 | 5/2014 |
| WO | 2014/127328 A2 | 8/2014 |
| WO | 2014/150851 A1 | 9/2014 |
| WO | 2015/016315 A1 | 2/2015 |
| WO | 2015/029691 A1 | 3/2015 |
| WO | 2015/127409 A1 | 8/2015 |
| WO | 2016145434 A1 | 9/2016 |
| WO | 2017/117292 A1 | 7/2017 |
| WO | 2018218250 | 11/2018 |
| WO | 2019217704 A1 | 11/2019 |

OTHER PUBLICATIONS

Nielsen, P. et al., "Sequence-Selective Recognition of DNA by Strand Displacement with a Thymine-Substituted Polyamide," Science, vol. 254, Iss. 5037, Dec. 6, 1991, pp. 1497-1500.

Seo et al, Four-color DNA sequencing by synthesis on a chip using photocleavable fluorescent nucleotides, 2005, PNAS, 102, 5926-5931.

Golubev, O. et al., "Formation of Mixed-Ligand Complexes of Pd2+ with Nucleoside 5'-Monophosphates and Some Metal-Ion-Binding Nucleoside Surrogates," Molecules, Oct. 22, 2014, vol. 19, No. 10, pp. 16976-16986.

Rothberg, J. et al., "An Integrated Semiconductor Device Enabling Non-Optical Genome Sequencing," Nature, vol. 475, Jul. 21, 2011, pp. 348-352.

Roy, B. et al., "Recent Trends in Nucleotide Synthesis," Chemical Reviews, 116(14), Jun. 20, 2016, pp. 7854-7897.

Shirai, M. et al., "Photoacid and Photobase Generators: Chemistry and Applications to Polymeric Materials," Progress in Polymer Science, vol. 21, Iss. 1, 1996, pp. 1-45.

Singh, Y. et al., "Recent Developments in Oligonucleotide Conjugation," Chemical Society Reviews, Iss. 6, Apr. 14, 2010, pp. 2054-2070.

Alawode, O. E. et al., "Clean Photodecomposition of 1-Methyl-4-Phenyl-1HTetrazole-5(4H)-Thiones to Carbodiimides Proceeds Via a Biradical," The Journal of Organic Chemistry, Jan. 7, 2011, pp. 216-222, vol. 76, No. 1.

Arimitsu K. et al., "Development of Highly Sensitive Photoreactive Materials Utilizing Photobase-generating Reactions and Base Proliferation Reactions", Journal Of Synthetic Organic Chemistry Japan, Jan. 1, 2012, pp. 508-516, vol. 70(5), Yuki Gosei Kagaku Kaokai, Tokyo, JP (with English Abstract).

Balakirev, M et al., "Photochemical Patterning of Biological Molecules Inside a Glass Capillary," Analytical Chemistry, vol. 77, No. 17, Sep. 1, 2005, pp. 5474-5479.

Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.

Beyer et al., "Combinatorial Synthesis of Peptide Arrays Onto a Microchip," Science, Dec. 21, 2007, p. 1888, vol. 318, 1 page and Sci. vol. 318 p. 1888 supporting online material, 6 pp.

Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.

Camarero, J., "Recent Developments in the Site-Specific Immobilization of Proteins Onto Solid Supports," Biopolymers, 2008, pp. 450-458, vol. 90, No. 3.

Carra, C. et al., "Proton-Coupled Electron Transfer in a Model for Tyrosine Oxidation in Photosystem II," Journal of the American Chemical Society, 2003, pp. 10429-10436, vol. 125.

Chen, "Solid-Phase Peptide Synthesis (SPPS) and Applications of Synthetic Peptides," Proteomics 2010, Jan. 2010, 63 pages [Online] [Retrieved on Sep. 16, 2015] Retrieved from the Internet<URL:http://bas.niu.edu.tw/download.php?filename=12155_cf09f16c.ppt&dir=communicty_forum/31&title=Topic+10-SPPS>.

Choung, R.S. et al., "Determination of B-Cell Epitopes in Patients with Celiac Disease: Peptide Microarrays," PLOS One, Jan. 29, 2016, e0147777, pp. 1-16, vol. 11, No. 1.

"Compound Summary for: CID 44140593, Tris(2,2'-bipyridine)ruthenium(II) dichloride," PubChem Compound, 2009 [Retrieved from the Internet Jun. 29, 2014: <http://pubchem.ncbi.nlm.gov.summary/summary.cgi?cid=44140593&loc=ec res>.

Fathalla, E., et al., "Efficient Synthesis of 1-Substituted-4-phenyl-1, 4-dihydro-SH-tetrazole-5-thione and (1-Phenyl-1H-tetrazol-5-yl)thiozcetyl Derivatives," Heteroatom Chemistry, 2007, vol. 18, No. 6, pp. 637-643.

Fan et al., Polyglutamine (PolyQ) diseases genetics to treatments Cell Transplant 23: 441-458, 2014.

Gomez-Zavaglia, A., et al., "Molecular structure, vibrational spectra and photochemistry of 5-mercapto-1-methyltetrazole," Journal of Molecular Structure, 2006, vol. 786, pp. 182-192.

Gunda, N. et al., "Micro-Spot with Integrated Pillars (MSIP) for Detection of Dengue Virus NS1," Biomed Microdevices, vol. 15, 2013, pp. 959-971.

Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet <URL: http://krex.kstate.edu/dspace/handle/2097/12022>.ex.kstate.edu/dspace/handle/2097/12022>, 2 pages.

Han, S-Y. et al., "Recent Development of Peptide Coupling Reagents in Organic Synthesis," Tetrahedron, 2004, pp. 2447-2467, vol. 60.

Lim, J-H. et al., "Direct-Write Dip-Pen Nanolithography of Proteins on Modified Silicon Oxide Surfaces," Angewandte Chemie International Edition, Wiley—VCH Verlag Gmbh & Co., May 25, 2003, pp. 2309-2312, vol. 42, No. 20.

Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).

Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.

Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.

Pellois, J.P. et al., "Individually Addressable Parallel Peptide Synthesis on Microchips". Nature Biotechnology, Sep. 2002, pp. 922-926, vol. 20, No. 9.

Piehler, J. et al., "Protein Interactions in Covalently Attached Dextran Layers," Colloid and Surfaces B: Biointerfaces 13 (1999), pp. 325-336.

Resch-Genger et al., "Quantum Dots Versus Organic Dyes as Fluorescent Labels," Nature Methods, Sep. 2008, pp. 763-775, vol. 5, No. 9.

Sardesai, N.P. et al., "A Microfluidic Electrochemiluminescent Device for Detecting Cancer Biomarker Proteins," Anal. Bioanal. Chem. Epub Jan. 11, 2013, pp. 3831-3138, vol. 405, No. 11.

Shin, D-S. et al., "Automated Maskless Photolithography System for Peptide Microarray Synthesis on a Chip," J. Comb. Chem., 2010, pp. 463-464 71, vol. 12.

Sun, X. et al., "Bicyclic Guanidinium Tetraphenylborate: A Photobase Generator and a Photocatalyst for Living Anionic Ring-Opening Polymerization and Cross-Linking of Polymeric Materials Containing Ester and Hydroxy Groups," Journal of the American Chemical Society, Jul. 2008, pp. 8130-8131, vol. 130, No. 26.

Suyama K. et al., "Photobase Generators: Recent Progress and Application Trend in Polymer Systems", Progress In Polymer Science, Feb. 1, 2009, pp. 194-209, vol. 34(2), Pergamon Press, Oxford, GB.

(56) References Cited

OTHER PUBLICATIONS

Tapia, V. et al., "Evaluating the Coupling Efficiency of Phosphorylated Amino Acids for SPOT Synthesis," J. Peptide Sci., 2008, pp. 1309-1314, vol. 14, No. 12.

Takahashi et al., Polyglutamne diseases: Where does toxicity come from? What is Toxicity? Where are we going? (J Mol Cell Biol 2: 180-191, 2010.

Thermofisher Scientific, "Molecular Probes™ Handbook: A Guide to Fluorescent Probes and Labeling Technologies," 11th edition, 2010, pp. 170-188.

Uddayasankar, U., "Towards a Surface Microarray Based Multiplexed Immunoassay on a Digital Microfluidics Platform," 2010, pp. 1-69, Master of Science Thesis. [Retrieved from the Internet Jun. 29, 2014: <https://cipweb.cardinal-ip.com/PCTSRS/PCTSRS DAT A/PCT-US%2014-16737/PRIOR_ART PCTPCTUS14-16737 UddavasankarMaster Thesis 2010.pdf>.

Wagner, "Quality Control for Peptide Chip Array Production," PhD Thesis, 2011, 140 pages, [Online] [Retrieved on Jun. 14, 2013] Retrieved from the Internet<URL:http://archiv.ub.uni-heidelberg.de/volltextserver/12602/1/report.pdf>.

Wang et al, Microfluidic DNA microarray analysis: A review, 2011, Analytica Chimica Acta, 687, 12-27.

Wei, H. et al., "Electrochemiluminescence of tris(2, 2'-bipyridyl)ruthenium and Its Applications in Bioanalysis: A Review," Luminescence, Mar.-Apr. 2011, pp. 77-85, vol. 26, Issue 2.

Young, J.D. et al., "Coupling Efficiencies of Amino Acids in the Solid Phase Synthesis of Peptides," Peptide Research, Jul. 1990, pp. 194-200, vol. 3, No. 4.

Yuan et al., "Integrated Tyramide and Polymerization-Assisted Signal Amplification for a Highly-Sensitive Immunoassay," Anal. Chem., 2012, pp. 10737-10744, vol. 84, No. 24.

Zhao, Y. et al., "A Fluorescent Amino Acid Probe to Monitor Efficiency of Peptide Conjugation to Glass Surfaces for High Density Microarrays," Mol. Biosyst., Epub Jan. 13, 2012, pp. 879-887, vol. 8, No. 3.

Uhlmann E., "Peptide nucleic acids (PNA) and PNA-DNA chimeras: from high binding affinity towards biological function", Biol Chem, 1998, vol. 379, No. 8-9, pp. 1045-1052.

PCT/US2019/031555—International Preliminary Report on Patentability, Nov. 19, 2020, 10 pages.

PCT/US2019/031555—International Search Report and Written Opinion, Jul. 10, 2019, 11 pages.

Ucar, Ultraviolet (UV) Radiation, Center for Science Education, Jan. 3, 2017. (Year: 2017).

Zivic, N., et al., "Recent Advances and Challenges in the Design of Organic Photoacid and Photobase Generators for Polymerizations", 2019, Angew. Chem. Int. Ed. 2019, 58, 10410-10422.

\* cited by examiner

Step 1- Reaction of acetate with phenylacetate

Step 2- Cascade/acid production

METHODS OF SYNTHESIZING A POLYNUCLEOTIDE ARRAY USING PHOTOACTIVATED AGENTS

CROSS-REFERENCE TO RELATED APPLICATIONS

This application claims the benefit of U.S. Provisional Application No. 62/668,964, filed May 9, 2018, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 6, 2020, is named VIB-023WO_SL.txt and is 1,488 bytes in size.

BACKGROUND

Microarray technology is readily used in biological research as it provides unprecedented information on nucleic acids in a wide range of applications such as gene expression and genotyping. In general, there are challenges associated with synthesizing polynucleotides as a result of incomplete deprotection reactions or unwanted reactions, such as depurination.

When making arrays by stepwise photodirected monomer-by-monomer synthesis, the use of a strong photoacid for the deprotection reaction tends to lead to depurination of nucleic acids, while the use of a weaker photoacid can result in a high incidence of incomplete deprotection reactions. If the deprotection reaction at any point is incomplete, this reduces the yield of the correct sequence at the locations in the array, and leads to undesirable mixtures of products. As the synthetic cycle may need to be repeated many times at each location on an array, even a small decrease in reaction efficiency can result in a dramatic effect on total yield.

What is needed, therefore, are improved nucleic acid synthesis methods that improve the efficiency of the reaction and therefore the yield of full length synthesized polynucleotides.

SUMMARY OF THE INVENTION

Described herein are methods for synthesizing a polynucleotide having a pre-defined sequence. In some embodiments, such methods comprise providing a support comprising a protected nucleic acid at a first feature; contacting said support with a photoresist solution comprising a photoacid generator; exposing said support to a wavelength of light, wherein said photoacid generator generates a weak acid via a cascade reaction upon exposure to the wavelength of light, wherein said weak acid deprotects the nucleic acid at the first feature; and binding a protected nucleic acid to said deprotected nucleic acid at said first feature.

In some embodiments, said weak acid comprises acetic acid, carbonic acid, phosphoric acid, sulfonic acid, triflic acid, or benzoic acid.

In some embodiments, said photoacid generator comprises a 4-tert butyl phenyl acid.

In some embodiments, said photoacid generator comprises 4-tert butyl phenyl acetate and PGMEA.

In some embodiments, said photoacid generator comprises 4-tert butyl phenyl carbonate and a compound selected from the group consisting of: propylene carbonate, methyl phenyl carbonate, and PGMEA.

In some embodiments, said photoacid generator comprises 4-tert butyl phenyl phosphate and phenyl phosphate.

In some embodiments, said photoacid generator comprises 4-tert butyl phenyl sulfonate and a compound selected from the group consisting of: phenyl sulfate, 4 methyl phenyl sulfate, dimethyl sulfate, methyl trifluoromethane sulfonate, and methyl fluorosulfonate.

In some embodiments, said photoacid generator comprises 4-tert butyl phenyl triflate and phenyl trifluoromethane sulfonate.

In some embodiments, said photoacid generator comprises 4-tert butyl phenyl benzoate and phenyl benzoate.

In some embodiments, said protected nucleic acid comprises a DMT group.

In some embodiments, said DMT group is bound to said nucleic acid at a 5' carbon.

In some embodiments, said wavelength of light is about 350 nm.

In some embodiments, the method further comprises repeating said steps to synthesize a polynucleotide of an intended length and sequence.

In some embodiments, said support comprises at least 10, at least 100, at least 1,000 or at least 10,000 features comprising said protected nucleic acid.

Described herein are methods for synthesizing an array of polynucleotides each having a pre-defined sequence. In some embodiments, such methods comprise providing a support comprising an array of protected nucleic acids bound to the surface; contacting said support with a solution comprising a photoacid generator; exposing selected regions of said support to a wavelength of light, wherein said photoacid generator generates a weak acid via a cascade reaction upon exposure to the wavelength of light in order to deprotect the nucleic acid at each location exposed to said wavelength of light; and contacting said wafer with a selected incoming nucleotide to bind to said deprotected nucleic acids.

In some embodiments, said incoming nucleotide comprises a DMT protecting group.

In some embodiments, the method further comprises repeating said steps a sufficient number of times to generate an array of polynucleotides each having a pre-defined sequence and intended length.

Described herein is a method for coupling a nucleotide monomer to a polynucleotide bound to a support, the method comprising: (a) providing a support comprising a terminal nucleotide bound to the surface of said support at a first feature; (b) performing an in situ synthesis of an NPPOC protecting group on said terminal nucleotide; (c) exposing said support to a wavelength of light at said first feature to remove said NPPOC protecting group from said terminal nucleotide; and (d) contacting said support with an incoming protected nucleotide to bind said incoming protected nucleotide to said deprotected terminal nucleotide at said first feature.

In some embodiments, the method further comprises (e) deprotecting said incoming protected nucleic acid bound to said terminal nucleotide, then repeating steps (a)-(e) to bind a second incoming protected nucleic acid.

In some embodiments, the method further comprises repeating all steps a sufficient number of times to synthesize a polynucleotide of an intended length and sequence bound to said substrate.

In some embodiments, the method further comprises contacting said support with a photoresist solution comprising ITX before exposing said support to said wavelength of light.

In some embodiments, said wavelength of light is about 365 nm.

In some embodiments, said NPPOC protecting group is bound to the 5' carbon of said terminal nucleotide.

In some embodiments, providing said support comprising said terminal nucleotides comprises globally deprotecting said terminal nucleotides before performing said in situ NPPOC synthesis.

In some embodiments, performing an in situ synthesis of NPPOC comprises contacting said support with an NPPOC synthesis solution comprising 2-(2-nitrophenyl) propyl chloroformate and pyridine.

In some embodiments, said NPPOC synthesis solution further comprises 1-methyl-2-pyrrolidinone.

Described herein is a method for synthesizing an array of polynucleotides each having a pre-defined sequence, the method comprising: (a) providing a support comprising an array of protected nucleotides bound to the surface; (b) performing in situ synthesis of NPPOC protecting groups on said array of nucleotides; (c) selectively exposing said support to a wavelength of light to remove said NPPOC protecting group from said array of nucleotides where addition of a selected incoming nucleotide is desired; (d) contacting said array with said selected incoming nucleotide to bind to said deprotected nucleotides; and (e) repeating steps (c)-(e) a sufficient number of times to complete a layer of desired nucleotide addition, thereby synthesizing an array of polynucleotides each having a pre-defined sequence.

In some embodiments, the method further comprises (f) globally deprotecting said incoming nucleotide bound to said array of polynucleotides prior to in situ synthesis of NPPOC protecting groups.

In some embodiments, the method further comprises repeating steps (b)-(f) and globally deprotecting said incoming nucleotide bound to said array of polynucleotides prior to in situ synthesis of NPPOC protecting groups a sufficient number of times to generate an array of polynucleotides each having a pre-defined sequence and intended length.

In some embodiments, said selected incoming nucleotide comprises a protecting group.

In some embodiments, said protecting group is DMT.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention. The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
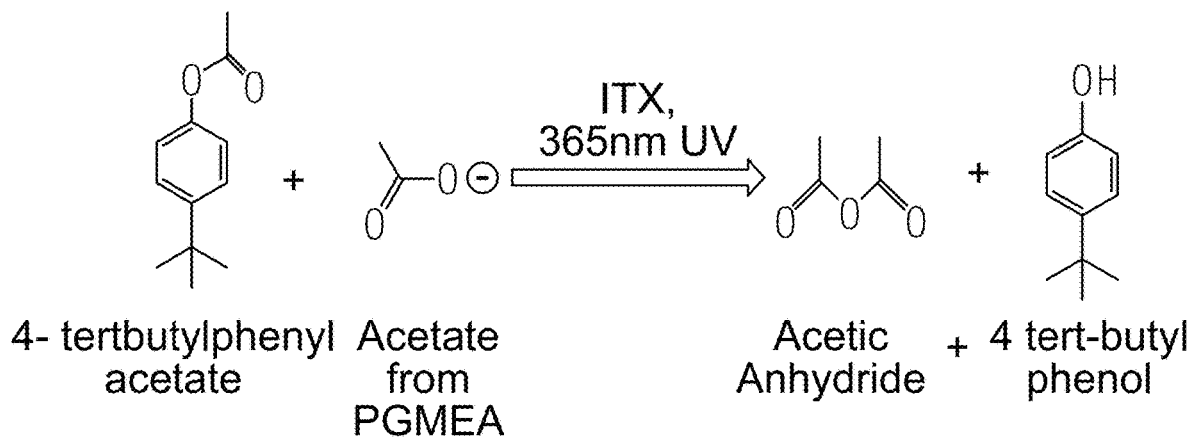
FIG. 1 illustrates an exemplary solvent-induced cascade photoacid system.
Figure 1:
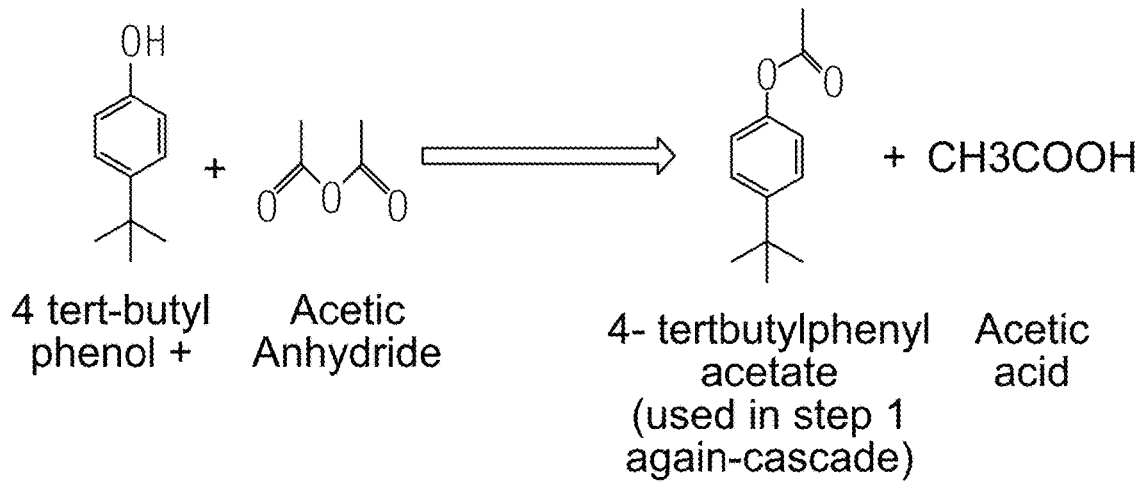

The details of various embodiments of the invention are set forth in the description below. Other features, objects, and advantages of the invention will be apparent from the description and the drawings, and from the claims.

Definitions

Terms used in the claims and specification are defined as set forth below unless otherwise specified.

As used herein, the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 μm to 775 μm.

As used herein, the term "photomask" or "reticle" or "mask" refers to an opaque plate with transparent patterns or holes that allow light to pass through. In a typical exposing process, the pattern on a photomask is transferred onto a photoresist.

As used herein, the term "photoresist" or "resist" or "photoactive material" refers to a light-sensitive material that undergoes a chemical modification, e.g., changes its solubility in a solution or generates a photoacid, when exposed to electromagnetic radiation, in particular ultra violet or deep ultra violet radiation. Photoresists includes organic or inorganic compounds.

As used herein the term "photoresist formulation" refers to a formulation including a photoactive compound and a photo-protective compound.

As used herein, the term "photoactive compound" refers to compounds that are modified when exposed to electromagnetic radiation. These compounds include, for example, cationic photoinitiators. For example, in preferred embodiments, the cationic photoinitiators are photoacid generators (PAGs), which generate a corresponding photoacid when exposed to electromagnetic radiation. Examples of photoactive compounds are disclosed in the International Patent Application No. PCT/US2013/070207, filed Nov. 14, 2013, which is incorporated herein in its entirety for all purposes. A photoinitiator is a compound especially added to a formulation to convert electromagnetic radiation into chemical energy in the form of initiating species, e.g., free radicals or cations. The acid or other product of a photoactive compound exposed to electromagnetic radiation may then react with another compound in a chain reaction to produce a desired chemical reaction. The spatial orientation of the occurrence of these chemical reactions is thus defined according to the pattern of electromagnetic radiation the solution or surface comprising photoactive compounds is exposed to. This pattern may be defined, e.g., by a photomask or reticle.

As used herein, the term "coupling molecule" or "monomer molecule" includes any natural or artificially synthesized nucleic acid optionally protected with a protecting group, such as DMT (4,4'-dimethoxytrityl) or NPPOC (3'-nitrophenylpropyloxycarbonyl).

As used herein, the term "coupling" or "coupling process" or "coupling step" refers to a process of forming a bond between two or more molecules such as a linking molecule or a coupling molecule.

As used herein, the term "coupling efficiency" refers to the probability of successful addition of a monomer to a reaction site (e.g., at the end of a polymer) available for binding to the monomer. For example, during the growth of a polynucleotide, an incoming nucleotide would bind to a deprotected terminal nucleotide bound to the surface of a wafer. It may be determined in bulk, e.g., by monitoring single monomer additions to several unique reaction sites simultaneously.

As used herein, the term "protecting group" includes a group that is introduced into a molecule by chemical modification of a functional group to obtain chemoselectivity in a subsequent chemical reaction. Chemoselectivity refers to directing a chemical reaction along a desired path to obtain a pre-selected product as compared to another. For example, the use of DMT as a protecting group enables chemoselectivity for polynucleotide synthesis using a light mask and a photoacid generator to selectively remove the protecting group and direct pre-determined nucleic acid coupling reactions to occur at locations defined by the light mask.

As used herein, the term "microarray," "array" or "chip" refers to a substrate on which a plurality of probe molecules of specific polynucleotide binding sequences have been synthesized at separate locations in an ordered manner thus forming an array. Specific polynucleotide sequences may be bound to the substrate of the chip through one or more different types of linker molecules. A "chip array" refers to a plate having a plurality of chips, for example, 24, 96, or 384 chips.

As used herein, the term "capping" or "capping process" or "capping step" refers to the addition of a molecule that prevents the further reaction of the molecule to which it is attached.

A "nucleotide" and a "nucleotide moiety" refer to a sub-unit of a nucleic acid (e.g., RNA, DNA, or an analogue thereof) which may include, but is not limited to, a phosphate group, a sugar group and a nitrogen containing base, as well as analogs of such sub-units. Other groups (e.g., protecting groups) can be attached to the sugar group and nitrogen-containing base group.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangeable in most instances. One skilled in the art would have the understanding that additional modification to the nucleoside may be necessary.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to, collectively, as "purine and pyrimidine bases and analogs thereof"). Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as levulinyl, acetyl, difluoroacetyl, trifluoroacetyl, isobutyryl, benzoyl, 9-fluorenylmethoxycarbonyl, phenoxyacetyl, dimethylformamidine, $N_1N$-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-rrethyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

A "nucleotide monomer" refers to a molecule which is not incorporated in a larger oligo- or poly-nucleotide chain and which corresponds to a single nucleotide sub-unit. Nucleotide monomers may also have activating or protecting groups, if such groups are necessary for the intended use of the nucleotide monomer.

A "polynucleotide" generally refers to a nucleotide multimer having any number of nucleotides greater than 1. The terms "oligonucleotide" and "polynucleotide" are often used interchangeably, consistent with the context of the sentence and paragraph in which they are used in.

A "polynucleotide intermediate" is a molecule occurring between steps in chemical synthesis of a polynucleotide, where the polynucleotide intermediate is subjected to further reactions to get the intended final product, for example a protected polynucleotide, which is then deprotected.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom (e.g., a sulfur atom, or the nitrogen atom of a mono- or di-alkyl amino group) or group (e.g., a methyl or other alkyl or functionalized alkyl groups).

A "group" includes both substituted and unsubstituted forms. Typical substituents include one or more lower alkyl, amino, imino, amido, alkylamino, arylamino, alkoxy, aryloxy, thioalkyl, alkylthio, arylthio, aryl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are typically chosen so as not to substantially adversely affect reaction yield (for example, not lower it by more than 20% (or 10%, or 5%, or 1%) of the yield otherwise obtained without a particular substituent or substituent combination). A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

A "protecting group" is used in the conventional chemical sense to reference a group, which reversibly renders unreactive a functional group under specified conditions of a desired reaction. Some protecting groups are well known to one skilled in the art. Examples of the protection/deprotection process as well as various protecting groups are described in Wuts and Greene, 2006, Greene's Protective Groups in Organic Synthesis, Wiley-Interscience, New York, N.Y. Any suitable protecting group known to one skilled in the art may be used. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

Overview

Described herein are compositions and methods for the synthesis of polynucleotides (e.g., DNA polynucleotides) in situ, on solid substrates. In particular, described herein are novel compositions and methods for the synthesis of arrays of polynucleotide probes in the form of DNA (micro)arrays, or DNA chips.

The laboratory procedures described below may, in part, employ methods well-known and commonly employed in the art. For example, standard techniques may be used for DNA and RNA isolation, purification, amplification, and cloning. Enzymatic reactions involving DNA ligase, DNA polymerase, restriction endonucleases, and the like may be performed according to the manufacturer's specifications. Such techniques and various other techniques may be generally performed according to Sambrook et al., 1989, Molecular Cloning—A Laboratory Manual, Cold Spring Harbor Laboratory Press, Cold Spring Harbor, N.Y.; Ausubel et al., 1993, Current Protocols in Molecular Biology, Volumes 1-3, John Wiley & Sons, Inc., New York, N.Y.; and Kriegler, 1990, Gene Transfer and Expression: A Laboratory Manual, Stockton Press, New York, N.Y., each of which is incorporated herein by reference in its entirety.

This application describes methods of sequence-specific synthesis of polynucleotides on a microarray platform through high throughput parallel synthesis using photolithography. Also described herein are nucleotide monomers and polynucleotide structures including nucleotide moieties, where the nucleotide monomers and nucleotide moieties each include various types of protecting groups. The nucleotide monomers and nucleotide moieties can be used in conjunction with methods, processes, and/or compositions of the present invention, for the deprotection of polynucleotides, in particular for polynucleotide synthesis on an array. Embodiments of the present invention enable quantitative or quasi-quantitative and rapid synthesis of the desired full-length polynucleotide product.

In various examples of the compositions and methods described herein, the schemes illustrating the synthesis of DNA polynucleotides are provided below.

Scheme I—Photoacid Cascade System for Nucleic Acid Synthesis

According to some embodiments, provided herein is a photoacid cascade system to facilitate efficient deprotection during nucleic acid synthesis. In standard nucleic acid synthesis, protecting groups, such as DMT, can be removed by exposure to acid. However, exposure to strong acids can result in depurination, while exposure to weak acids can result in incomplete deprotection, both of which harm the yield of the nucleotide synthesis reaction.

Provided herein are novel nucleotide synthesis reactions that show improved yields of polynucleotides synthesized on a microarray.

Provided herein, is a novel nucleotide synthesis reaction which uses a photoactivated cascade reaction to generate sufficient weak acid to improve yields of deprotection while avoiding depurination.

Photocascade System

In some embodiments, provided herein is a nucleotide synthesis reaction which uses a photoactivated cascade reaction to generate sufficient weak acid to improve yields of deprotection while avoiding depurination characteristic of strong acid deprotection. In some cases, the photoactivated cascade reaction comprises a reaction of acetate with phenylacetate.

FIG. 1 provides an exemplary photoacid cascade system useful for nucleotide synthesis. For this reaction, a solution of propylene glycol methyl ether acetate (PGMEA) comprising poly(methyl methacrylate) (PMMA), 4-tert butyl phenyl acetate, and isopropylthioxanthone (ITX) is prepared. In particular embodiments, a reaction of the 4-tert-butylphenyl acetate with the acetate from PGMEA is catalyzed by ITX upon exposure of the solution to light at a wavelength of 356 nm to generate acetic anhydride and 4 tert-butyl phenol as intermediate compounds. The acetic anhydride and 4-tert-buytl phenol then react to form the original reagent 4-tertbutylphenyl acetate and acetic acid. In this cascade reaction, acetic acid is thereby produced in the photoactivated solution upon exposure to 365 nm light. The acetic acid generated in the location of DMT-protected nucleotides may then react to deprotect the nucleotides with high efficiency.

In some embodiments the photoactive solution comprises about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% by weight PMMA. In preferred embodiments the photoactive solution comprises about 0.5-5% PMMA by weight. In more preferred embodiments the photoactive solution comprises about 1-3% PMMA by weight. In one embodiment, the photoactive solution comprises about 2% PMMA by weight.

In some embodiments the photoactive solution comprises about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% by weight 4-tert butyl phenyl acetate. In preferred embodiments the photoactive solution comprises about 2-7% 4-tert butyl phenyl acetate by weight. In more preferred embodiments the photoactive solution comprises about 3-6% 4-tert butyl phenyl acetate by weight. In one embodiment, the photoactive solution comprises about 5% 4-tert butyl phenyl acetate by weight.

In some embodiments the photoactive solution comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% by weight ITX. In preferred embodiments the photoactive solution comprises about 2-7% ITX by weight. In more preferred embodiments the photoactive solution comprises about 3-6% ITX by weight. In one embodiment, the photoactive solution comprises about 5% ITX by weight.

In particular embodiments, the photoactive solution comprises about 0.5-5% PMMA by weight, about 2-7% 4-tert butyl phenyl acetate by weight, and about 5% ITX by weight. In more particular embodiments, the photoactive solution comprises about 1-3% PMMA by weight, about 3-6% 4-tert butyl phenyl acetate by weight, and about 3-6% ITX by weight. In one embodiment, the photoactive solution comprises about 2% PMMA by weight, about 5% 4-tert butyl phenyl acetate by weight, and about 5% ITX by weight.

Although certain embodiments of a photoactivated cascade utilize a 4-tert butyl phenyl acetate-PGMEA system, other acid cascade systems can be used to generate a weak acid via a cascade system for site-specific deprotection. In some embodiments, a 4-tert butyl phenyl carbonate-Propylene carbonate photoactivated acid cascade system is used to produce carbonic acid/acetic acid. In some embodiments, a 4-tert butyl phenyl carbonate-Methyl phenyl carbonate photoactivated acid cascade system is used to produce carbonic acid/acetic acid. In some embodiments, a 4-tert butyl phenyl carbonate-PGMEA photoactivated acid cascade system is used to produce carbonic acid/acetic acid. In some embodiments, a 4-tert butyl phenyl phosphate-Phenyl phosphate photoactivated acid cascade system is used to produce phosphoric acid. In some embodiments, a 4-tert butyl phenyl sulfonate-Phenyl sulfate photoactivated acid cascade system is used to produce Sulfonic acid. In some embodiments, a 4-tert butyl phenyl sulfonate-4 methyl phenyl sulfate photoactivated acid cascade system is used to produce Sulfonic acid. In some embodiments, a 4-tert butyl phenyl sulfonate—Dimethyl sulfate photoactivated acid cascade system is used to produce Sulfonic acid. In some embodiments, a 4-tert butyl phenyl sulfonate-Methyl trifluoromethane sulfonate photoactivated acid cascade system is used to produce Sulfonic acid. In some embodiments, a 4-tert butyl phenyl sulfonate-Methyl fluorosulfonate photoactivated acid cascade system is used to produce Sulfonic acid. In some embodiments, a 4-tert butyl phenyl triflate—Phenyl trifluoromethane sulfonate photoactivated acid cascade system is used to produce Triflic acid. In some embodiments, a 4-tert butyl phenyl benzoate—Phenyl benzoate photoactivated acid cascade system is used to produce Benzoic acid.

DMT Deprotection and Monomer Coupling Using a Photoactivated Acid Cascade

Figure 2:
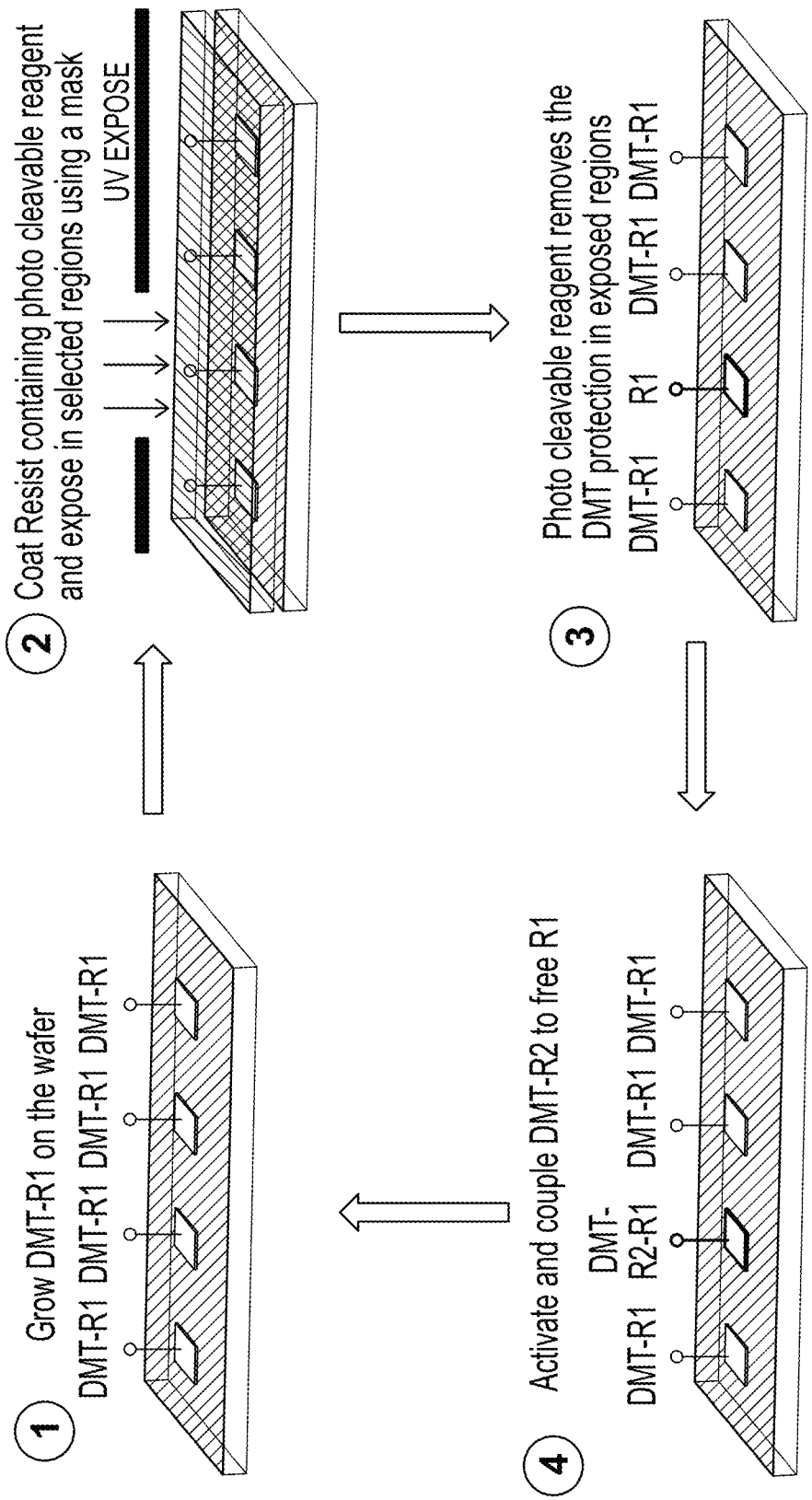
FIG. 2 shows an exemplary method for sequence-specific synthesis of a polynucleotide microarray using a solvent-induced cascade photoacid system to deprotect protected terminal nucleotides bound to a wafer.

Polynucleotides can be efficiently synthesized on an array using a photoactivated acid cascade solution as described herein. FIG. 2 illustrates an exemplary method for array polynucleotide synthesis.

As shown in FIG. 2, a wafer comprising 4,4'-dimethoxytrityl (DMT) protected nucleotides may be provided. A photoactivated acid cascade solution may be coated on the surface of the wafer. Light may be locally applied to selected regions where addition of a selected nucleotide is required for nucleotide synthesis. In some embodiments, light is applied through the use of a photomask. The wafer with the photoactivated solution can be exposed to a wavelength of light to initiate the acid cascade reaction, which deprotects DMT-protected nucleotides in the locations where the wafer is exposed to light. In some embodiments, the wafer is exposed to light for 500 ms per field. In some embodiments, after exposure is completed, a post exposure delay time before washing is performed at room temperature for 10 minutes. After deprotection, the photoactivated solution may be washed from the surface, leaving a wafer with selected molecules that have a deprotected nucleotide. A desired nucleotide may then be added to the wafer to couple with the deprotected nucleotides. In preferred embodiments, the incoming nucleotide is DMT protected to allow subsequent cycles of nucleotide addition according to the reaction scheme provided. To prevent synthesis on deprotected molecules that did not bind to an incoming nucleotide, a capping solution can be applied to the wafer.

The above cycle can be repeated as many times as required to synthesize the desired polynucleotide sequences at each location on the array.

In some embodiments, the post exposure delay time is about 0.5 minutes, 1 minute, 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes, 10 minutes, 10.5 minutes, 11 minutes, 11.5 minutes, 12 minutes, 12.5 minutes, 13 minutes, 13.5 minutes, 14 minutes, 14.5 minutes, or 15 minutes. In preferred embodiments, the post exposure delay time is about 3-6 minutes.

Scheme 2—In Situ NPPOC Synthesis

Figure 3:
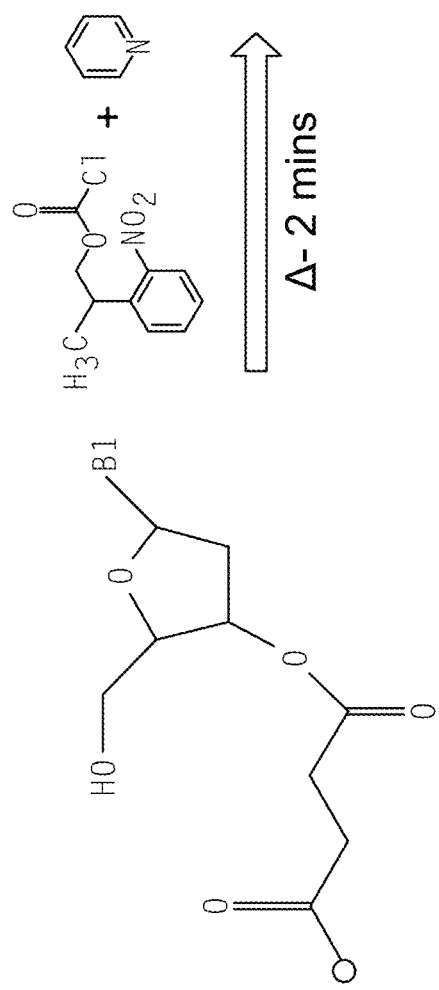
FIG. 3 illustrates an exemplary reaction scheme for in situ synthesis of an NPPOC ((3'-nitrophenylpropyloxycarbonyl)-protected terminal nucleotide.
Figure 3:
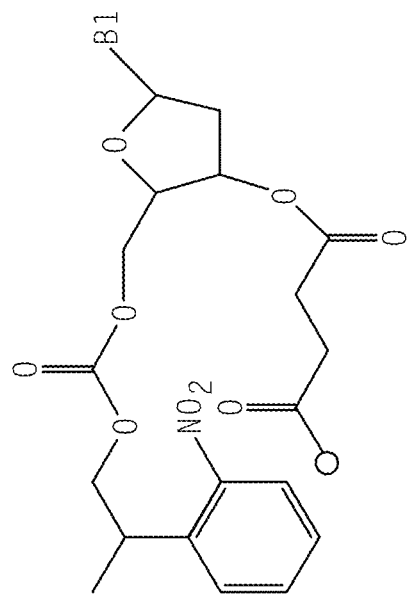

In some embodiments, the polynucleotide synthesis scheme relies on in situ synthesis of 3'-nitrophenylpropyloxycarbonyl (NPPOC) protecting groups for a free nucleotide bound to an array. An example of a reaction scheme for in situ synthesis of NPPOC is shown in FIG. 3. As shown, a nucleotide with an unprotected 5' hydroxyl group can be converted to an NPPOC-protected nucleotide by addition of a in situ NPPOC synthesis solution containing 2-(2-Nitrophenyl) propyl chloroformate dissolve in 1-Methyl-2-Pyrrolidinone and Pyridine.

Figure 4:
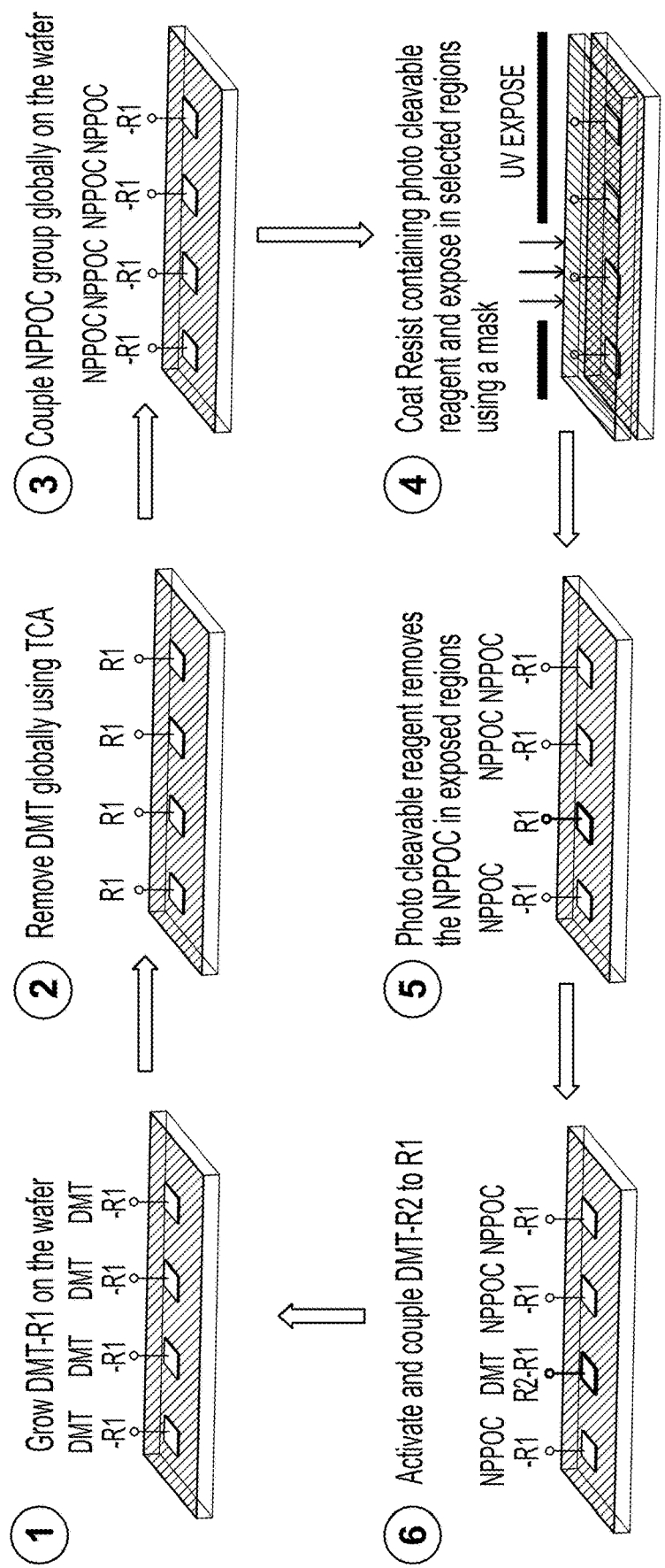
FIG. 4 shows an exemplary synthesis of a polynucleotide microarray using an in-situ reaction to add an NPPOC protecting group to the terminal nucleotides at each feature, followed by a two-step photoactivated NPPOC deprotection reaction and nucleotide addition reaction, according to an embodiment of the invention.
Figure 5:
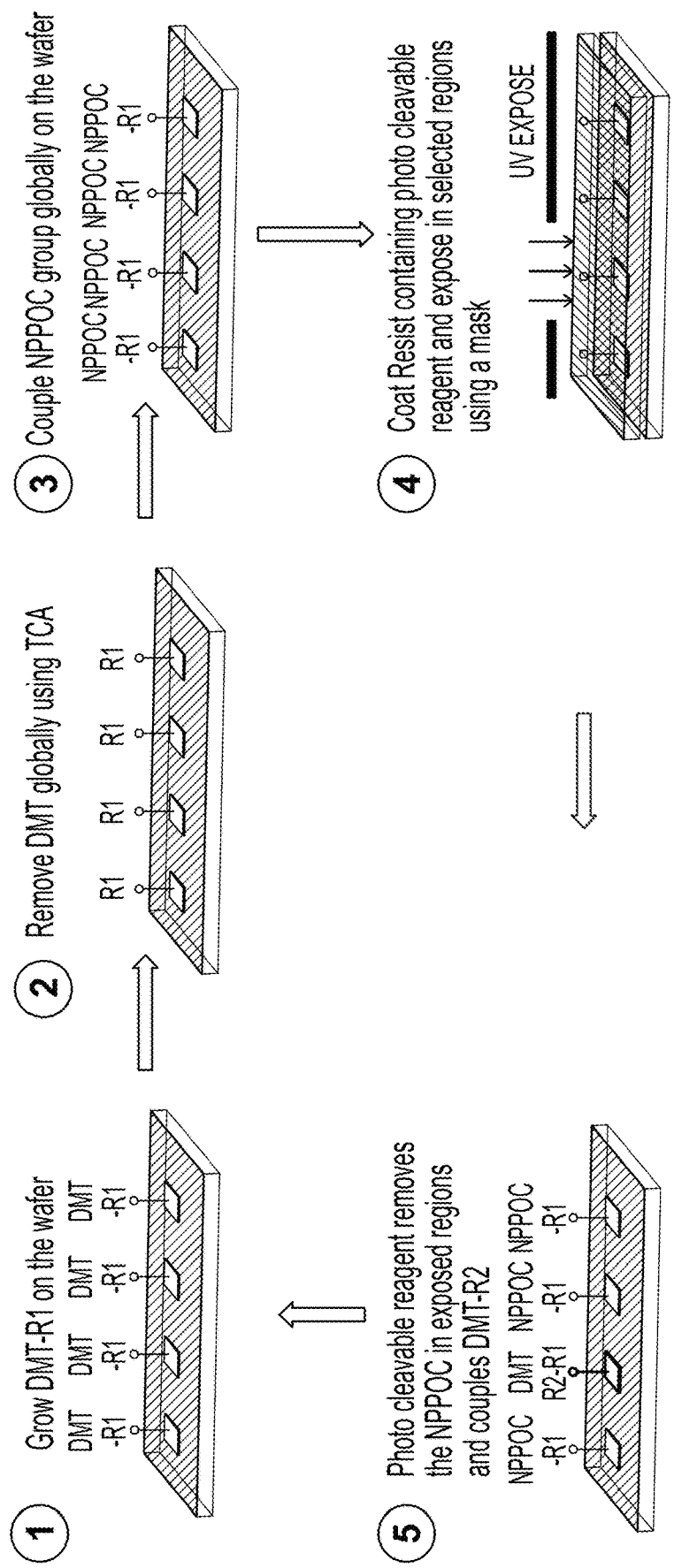
FIG. 5 shows an exemplary synthesis of a polynucleotide microarray using an in-situ reaction to add an NPPOC protecting group to the terminal nucleotides at each feature, followed by a one-step photoactivated NPPOC deprotection and nucleotide addition reaction, according to an embodiment of the invention.

Thus, for both one-step and two-step NPPOC protected polynucleotide synthesis schemes, NPPOC-protected nucleotides can be prepared, according to some embodiments, as follows: As shown in FIG. 4 and FIG. 5, a wafer comprising DMT protected nucleotides (DMT-R1) is provided. The DMT protecting group is then globally removed using a strong acid, such as TCA. NPPOC is then coupled to the deprotected nucleotides according to the reaction scheme as shown in FIG. 3. In some embodiments, in situ synthesis of NPPOC to each of the deprotected bound to the wafer is performed by spin coating an in situ NPPOC synthesis solution comprising 0.3M 2-(2-nitrophenyl) propyl chloroformate dissolved in a solvent of 30% 1-methyl-2-pyrrolidinone and 70% pyridine onto the wafer. The wafer can then be baked at 95° C. for two minutes to globally couple the NPPOC protecting group to the deprotected nucleotides bound to the wafer. The wafer can then be stripped with 1-methyl-2-pyrrolidinone and isopropyl alcohol.

From the resulting array of NPPOC-protected nucleotides, addition of selected nucleotides at each spot can proceed according to one-step or two-step NPPOC deprotection and coupling as described herein. In some embodiments, once a layer of protected nucleotides has been added to the nucleotides bound to the array as desired, the global deprotection and NPPOC synthesis can be repeated as many times as necessary to achieve the desired polynucleotide sequence lengths at each location on the wafer.

In some embodiments, the array coated with the NPPOC synthesis solution is baked at 65° C., 70° C., 75° C., 80° C., 85° C., 90° C., 95° C., 100° C., 105° C., or 110° C. In preferred embodiments, the array coated with the NPPOC synthesis solution is baked at a temperature between about 80-100° C. In some embodiments, the array coated with the NPPOC synthesis solution is baked for about 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, 190 seconds, 200 seconds, 210 seconds, 220 seconds, 230 seconds, 240 seconds, 250 seconds, 260 seconds, 270 seconds, 280 seconds, 290 seconds, 300 seconds, 310 seconds, 320 seconds, 330 seconds, 340 seconds, 350 seconds, or 360 seconds. In preferred embodiments, the array coated with the NPPOC synthesis solution is baked for about 60-240 seconds. In particular embodiments, the array coated with the NPPOC synthesis solution is baked for about 120 seconds. In particular embodiments, the array coated with the NPPOC synthesis solution is baked at a temperature between about 80-100° C. for about 60-240 seconds. In one embodiment, the array coated with the NPPOC synthesis solution is baked at about 95° C. for about 120 seconds.

In some embodiments, the concentration of 2-(2-Nitrophenyl) propyl chloroformate in the in situ NPPOC synthesis solution is about 0.01M, 0.02M, 0.03M, 0.04M, 0.05M, 0.06M, 0.07M, 0.08M, 0.09M, 0.1M, 0.11M, 0.12M, 0.13M, 0.14M, 0.15M, 0.16M, 0.17M, 0.18M, 0.19M, 0.2M, 0.21M, 0.22M, 0.23M, 0.24M, 0.25M, 0.26M, 0.27M, 0.28M, 0.29M, 0.3M, 0.31M, 0.32M, 0.33M, 0.34M, 0.35M, 0.36M, 0.37M, 0.38M, 0.39M, 0.4M, 0.41M, 0.42M, 0.43M, 0.44M, 0.45M, 0.46M, 0.47M, 0.48M, 0.49M, 0.50M, 0.51M, 0.52M, 0.53M, 0.54M, 0.55M, 0.56M, 0.57M, 0.58M, 0.59M, 0.6M 0.61M, 0.62M, 0.63M, 0.64M, 0.65M, 0.66M, 0.67M, 0.68M, 0.69M, 0.7M, 0.71M, 0.72M, 0.73M, 0.74M, 0.75M, 0.76M, 0.77M, 0.78M, 0.79M, 0.8M, 0.81M, 0.82M, 0.83M, 0.84M, 0.85M, 0.86M, 0.87M, 0.88M, 0.89M, 0.90M, 0.91M, 0.92M, 0.93M, 0.94M, 0.95M, 0.96M, 0.97M, 0.98M, 0.99M, or 1.0M. In preferred embodiments the concentration of 2-(2-Nitrophenyl) propyl chloroformate in the in situ NPPOC synthesis solution is about 0.05-0.8M. In more preferred embodiments the concentration of 2-(2-Nitrophenyl) propyl chloroformate in the in situ NPPOC synthesis solution is about 0.2-0.5M.

In some embodiments, the 2-2-(2-Nitrophenyl) propyl chloroformate is dissolved in a solution comprising the following percentages of 1-methyl-2-pyrrolidinone and pyridine as provided in Table 1 to form the NPPOC synthesis solution:

TABLE 1

Solvent constitution for the in situ NPPOC synthesis solution

| 1-Methyl-2-Pyrrolidinone (%) | Pyridine (%) |
| --- | --- |
| 0 | 100 |
| 1 | 99 |
| 2 | 98 |
| 3 | 97 |
| 4 | 96 |
| 5 | 95 |
| 6 | 94 |
| 7 | 93 |
| 8 | 92 |
| 9 | 91 |
| 10 | 90 |
| 11 | 89 |
| 12 | 88 |
| 13 | 87 |
| 14 | 86 |
| 15 | 85 |
| 16 | 84 |
| 17 | 83 |
| 18 | 82 |
| 19 | 81 |
| 20 | 80 |
| 21 | 79 |
| 22 | 78 |
| 23 | 77 |
| 24 | 76 |
| 25 | 75 |
| 26 | 74 |
| 27 | 73 |
| 28 | 72 |
| 29 | 71 |
| 30 | 70 |
| 31 | 69 |
| 32 | 68 |
| 33 | 67 |
| 34 | 66 |
| 35 | 65 |
| 36 | 64 |
| 37 | 63 |
| 38 | 62 |
| 39 | 61 |
| 40 | 60 |
| 41 | 59 |
| 42 | 58 |
| 43 | 57 |
| 44 | 56 |
| 45 | 55 |
| 46 | 54 |
| 47 | 53 |
| 48 | 52 |
| 49 | 51 |
| 50 | 50 |
| 51 | 49 |
| 52 | 48 |
| 53 | 47 |
| 54 | 46 |
| 55 | 45 |
| 56 | 44 |
| 57 | 43 |
| 58 | 42 |
| 59 | 41 |
| 60 | 40 |
| 61 | 39 |
| 62 | 38 |
| 63 | 37 |
| 64 | 36 |

TABLE 1-continued

Solvent constitution for the in situ NPPOC synthesis solution

| 1-Methyl-2-Pyrrolidinone (%) | Pyridine (%) |
|---|---|
| 65 | 35 |
| 66 | 34 |
| 67 | 33 |
| 68 | 32 |
| 69 | 31 |
| 70 | 30 |
| 71 | 29 |
| 72 | 28 |
| 73 | 27 |
| 74 | 26 |
| 75 | 25 |
| 76 | 24 |
| 77 | 23 |
| 78 | 22 |
| 79 | 21 |
| 80 | 20 |
| 81 | 19 |
| 82 | 18 |
| 83 | 17 |
| 84 | 16 |
| 85 | 15 |
| 86 | 14 |
| 87 | 13 |
| 88 | 12 |
| 89 | 11 |
| 90 | 10 |
| 91 | 9 |
| 92 | 8 |
| 93 | 7 |
| 94 | 6 |
| 95 | 5 |
| 96 | 4 |
| 97 | 3 |
| 98 | 2 |
| 99 | 1 |

In Situ NPPOC Protection and Two-Step Photoactivated Deprotection and Synthesis.

In some embodiments, in situ NPPOC protected nucleotides are deprotected and coupled to an incoming nucleotide (e.g., DMTR2) according to a two-step synthesis scheme, e.g., as shown in FIG. 4. Accordingly, a photoresist solution comprising ITX to facilitate photoactivated deprotection at selected sites on the array is coated on the surface of the wafer. The wafer is selectively exposed to light to selectively remove NPPOC from protected nucleotides bound to the array. The photoactivated solution is then washed off the wafer, and a solution comprising the desired nucleotide is added to the wafer to bind to deprotected nucleotides. In some embodiments, the incoming nucleotide is protected, e.g., has a 5' carbon bound to a DMT group. These steps can be repeated until the synthesis layer is complete (i.e., when no further additions to NPPOC-protected nucleotides are desired). Once the layer is complete, another round of synthesis steps can be performed, starting with global deprotection of protected nucleotides bound to the array, and followed by in situ NPPOC protection.

In Situ NPPOC Protection and One-Step Photoactivated Deprotection and Synthesis.

In some embodiments, in situ NPPOC protected nucleotides are deprotected and coupled to an incoming nucleotide according to a one-step synthesis scheme, e.g., as shown in FIG. 5. Accordingly, a photoresist solution comprising ITX to facilitate photoactivated deprotection at selected sites on the array is coated on the surface of the wafer and selectively exposed to light to selectively deprotect nucleotides bound to the array. The photoresist solution may also comprise the desired nucleotide to bind to deprotected nucleotides so that deprotection and incoming nucleotide coupling can occur in a single step. In some embodiments, the incoming nucleotide is protected, e.g., has a 5' carbon bound to a DMT group. These steps can be repeated until the synthesis layer is complete (i.e., when no further additions to NPPOC-protected nucleotides are desired). Once the layer is complete, another round of synthesis steps can be performed, starting with global deprotection of protected nucleotides bound to the array, and followed by in situ NPPOC protection.

Wafer Functionalization

In some embodiments, a wafer comprising an array of protected nucleotides bound to the surface of a wafer, preferably via a linker, is provided to facilitate polynucleotide synthesis. In some embodiments, provided herein are wafers functionalized to facilitate polynucleotide synthesis.

Wafer Functionalization Scheme

In some embodiments, wafers are functionalized according to the following reaction scheme:
1. Functionalize wafer with an amine group (e.g., using an organofunctional alkoxysilane).
2. Attach a linker to the amine group of the functionalized wafer. The linker may comprise a protected amine group. The linker may further comprise a carboxyl group. In some embodiments, the carboxyl group of the linker attaches to the amine group of the functionalized wafer. In some embodiments, the attachment binds the linker to the functionalized wafer.
3. Deprotect the amine group on the bound linker.
4. Bind the amine group to a modified DMT-protected nucleotide, e.g., a DMT-protected phosphoramidite. This may result in an array with DMT-R1 bound to the wafer.

In one embodiment, the functionalize reaction scheme is as follows:
1. Functionalize wafer with amine groups by adding 3-Aminopropyl triethoxysilane (APTES)
2. Couple free amines to FMOC-NH-PEG6-CH2CH2COOH—resulting in Fmoc protected linkers bound to the surface of the wafer
3. Remove Fmoc from the amine group with 4-methyl piperidine
4. Add DMT-phosphoramidite thymine CED-5' cyanoethyl (DMT protected phosphoramidite group to allow coupling of next nucleic acid)
5. Cap unbound linkers
6. Perform photoacid cascade system as described herein.

Organofunctional Alkoxysilane

As shown, a silicon dioxide wafer can be functionalized by coating with a compound comprising a free amine group for subsequent binding. In some embodiments, the wafer is coated with organofunctional alkoxysilane molecules. In some embodiments, the wafer is coated with APTES. In some embodiments, a solution of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% by weight APTES is used. In some embodiments, a solution of about 0.1-5.0% by weight APTES is used. In preferred embodiments, a solution of about 0.5-4.0% by weight APTES is used. In yet more preferred embodiments, a solution of about 1.0-3.0% by weight APTES is used. In one embodiment, a solution of about 2.0% by weight APTES is used.

Linker

In some embodiments, a linker is bound to the wafer coated with free amine groups. In some embodiments, the linker comprises a carboxylic acid group to bind to the free amine group. In some embodiments, the linker further comprises a chain to facilitate spacing between the surface and the synthesized polynucleotide. The chain may comprise one or more PEG groups linked together. In some embodiments, the chain may comprise an aliphatic carbon chain. In some embodiments, the linker further comprises a group to facilitate binding of a nucleotide (e.g., a phosphoramidite). In some embodiments, the group to facilitate binding of the nucleotide is an amine group. In some embodiments, the amine group to facilitate binding of the nucleotide is a protected amine group, such as an Fmoc-protected amine group. In some embodiments, the linker comprises a carboxylic acid group on one end, an amine group to facilitate binding of the nucleotide on the other end, and a spacer molecule, such as one or more PEG groups or an aliphatic chain connecting the amine group to the carboxylic acid group. For example, the linker may comprise Fmoc-NH-PEG$_6$-CH$_2$CH$_2$COOH, where the carboxyl group binds to the wafer's surface-bound amine, and the Fmoc protected amine group can be deprotected for subsequent attachment of another molecule to facilitate polynucleotide synthesis. A protected amine group can be deprotected by a suitable reagent, such as one containing 4-methyl piperidine.

Phosphoramidite (DMT Protected)

In some embodiments, to generate a functionalized array with a series of DMT-protected nucleotides bound to a wafer, a modified DMT-protected nucleoside is bound to a free amine bound to the surface of the array. In some embodiments, the amine group must first be deprotected to facilitate binding of the DMT-protected nucleotide. In some embodiments, the amine group is at the end of a linker bound to the surface of the array.

In some embodiments, thymine CED-5' cyanoethyl is bound to free amine groups bound to the surface of the wafer, although phosphoramidites with other bases can be used.

Formulations

Disclosed herein are formulations such as photoresist formulations, displacement formulations, activating formulations, and linker formulations. These formulations can be useful in the manufacture and/or use of, e.g., polynucleotide microarrays disclosed herein.

Photoresist Formulations

Disclosed herein are photoresist formulations comprising a photoactive compound and a photo-protective compound. In some embodiments, the photoactive compound is a photoacid generator. Exposure of the photoactive compounds to electromagnetic radiation may induce a photochemical event that produces a compound that goes on to induce material transforming secondary reactions within a diffusion-limited radius. A photoresist formulation may comprise a photoactive compound comprising a radiation-sensitive catalyst precursor, e.g., a photoacid generator (PAG); a plurality of chemical groups that can react by elimination, addition, or rearrangement in the presence of catalyst; and optional additives to improve performance or processability, e.g., surfactants, photosensitizers, and etch resistors.

In some embodiments, the photoacid generator is a cationic photoinitiator. A photoinitiator may be added to a formulation to convert absorbed light energy, UV or visible light, into chemical energy in the form of initiating species, e.g., free radicals or cations. The ability of some types of cationic photo initiators to serve as latent photochemical sources of very strong protonic or Lewis acids is generally the basis for their use in photo imaging applications. In some embodiments, a photoacid generator is an iodonium salt, a polonium salt, or a sulfonium salt. In some embodiments, a photoacid generator is (4-Methoxyphenyl) phenyliodonium or trifluoromethanesulfonate. In some embodiments, a photoacid generator is (2,4-dihydroxyphenyl)dimethylsulfonium triflate or (4 methoxyphenyl)dimethylsulfonium triflate, shown below:

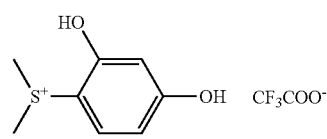

In some embodiments, a photoacid generator is iodonium and sulfonium salts of triflates, phosphates and/or antimonates. In some embodiments, a photoacid generator is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0% of the total formulation concentration. In some embodiments, a photoacid generator is about 0.5-5% by weight of the total photoresist formulation concentration.

In some embodiments, the photo-protective compound is titanium dioxide, zinc sulfide, magnesium fluoride, and the like.

In some embodiments, a photoresist formulation further includes a polymer and a solvent.

In some embodiments, the polymer is poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly(acrylic acid), poly(sodium styrene sulfonate), poly(-acrylamido-2-methyl-1-propanesulfonic acid), polysaccharides, and cellulose derivatives.

In some embodiments, a polymer is a non-crosslinking inert polymer. In some embodiments, a polymer is a polyvinyl pyrrolidone. The general structure of polyvinyl pyrrolidone is as follows, where n is any positive integer greater than 1:

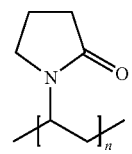

In some embodiments, a polymer is a polymer of vinyl pyrrolidone. In some embodiments, a polymer is polyvinyl pyrrolidone. Poly vinyl pyrrolidone is soluble in water and other polar solvents. When dry it is a light flaky powder, which generally readily absorbs up to 40% of its weight in atmospheric water. In solution, it has excellent wetting properties and readily forms films. In some embodiments, a polymer is a vinyl pyrrolidone or a vinyl alcohol. In some embodiments, a polymer is a polymethyl methacrylate.

In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some embodiments, a polymer is about 0.5-5% by weight of the total formulation concentration. In some embodiments, a polymer is 2.5-5% by weight of the total formulation concentration.

In some embodiments, a photoresist formulation includes a photoacid generator and a photo sensitizer in a polymer matrix dispersed in a solvent. In some embodiments, the polymer in the composition of the photoresist is generally inert and non-crosslinking but the photoactive compounds will readily generate sufficient quantities of photoacid upon exposure to electromagnetic radiation to bring about a desired reaction to produce a product at acceptable yield.

In some embodiments, the solvent is about 80-90 weight % of the total formulation concentration. In some embodiments, the solvent is about 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% of the total formulation concentration.

In some embodiments, a solvent is water, ethyl lactate, n methyl pyrrolidone or a combination thereof. In some embodiments, ethyl lactate is dissolved in water to more than 50% to form a solvent. In some embodiments, a solvent comprises about 10% propylene glycol methyl ether acetate (PGMEA) and about 90% DI water. In some embodiments, a solvent includes up to about 20% PGMEA. In some embodiments, a solvent comprises 50% ethyl lactate and 50% n methyl pyrrolidone. In some embodiments, a solvent is n methyl pyrrolidone. In some embodiments, a solvent is water, an organic solvent, or combination thereof. In some embodiments, the organic solvent is N Methyl pyrrolidone, di methyl formamide or combinations thereof. In some embodiments, the solvent is about 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration. In some embodiments, the solvent is about 80-90% by weight of the total formulation concentration.

In particular embodiments, the photoresist formulation comprises, by weight, about 0.5-5% photoacid generator, about 80-90% solvent, and about 0.1-5% polymer. In particular embodiments, the photoresist formulation comprises, by weight, about 0.5-5% photoacid generator, about 80-97% solvent, and about 2.5-5% polymer.

In particular embodiments, a photoresist formulation includes a photosensitizer, a photoactive compound, a polymer, and a solvent.

In some embodiments, the photoresist formulation forms a photoresist layer on the surface of a microarray.

Activating Formulations

Disclosed herein are activating formulations for activating carboxylic acid so that it reacts with a free amino group. In some embodiments, an activating formulation includes an activation agent (also referred to as a coupling reagent). In some embodiments, the coupling reagent is carbodiimide or triazole. In some embodiments, the carbodiimide is 1-ethyl-3-(3-dimethylaminopropyl) carbodiimide. In some embodiments, the carboxylic acid group activating compound is N-Hydroxysuccinimide (NHS). In some embodiments, the activating formulation optionally includes a solvent and/or a polymer.

In some embodiments, the activating formulation further includes an $R_2$-acetic acid, for example, bromoacetic acid, chloroacetic acid, fluoroacetic acid, iodoacetic acid. In some embodiments, the activating formulation further includes a coupling molecule, for example, DMT-protected nucleotide.

In some embodiments, the coupling reagent is selected from: 1-Ethyl-3-(3-dimethylaminopropyl)carbodiimide [EDC], N-hydroxysuccinimide [NHS], 1,3-Diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], and N,N-Diisopropylethylamine [DIEA]. In some embodiments, the solvent is water. In some embodiments, the solvent is N-methylpyrrolidone (NMP). In some embodiments, the coupling reagent converts the carboxylic acid to a carbonyl group (i.e., carboxylic acid group activation). In some embodiments, the carboxylic acid group is activated for about 5, 10, 15, 20, 30, 45, or 60 minutes after exposure to a displacement reaction formulation.

In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% by weight of the total formulation concentration. In some embodiments, a coupling reagent is about 0.5-5% by weight of the total formulation concentration. In some embodiments, a coupling reagent is 2-4% by weight of the total formulation concentration.

In any of the combinations above, the formulation can be completely water strippable. Thus, in some embodiments, water can be used to wash away the formulation after exposure.

In some embodiments, the activating formulation comprises 4% by weight of 1-ethyl-3-(3-dimethylaminopropyl) carbodiimide and 2% by weight of N-hydroxysuccinimide (NHS) dissolved in deionized water. In some embodiments, the activating formulation comprises 4% by weight of 1, 3-Diisopropylcarbodiimide (DIC) and 2% by weight of hydroxybenzotriazole (HOBt) dissolved in NMP. In some embodiments, the activating formulation comprises 4% by weight of (O-(7-azabenzotriazol-1-yl)-N,N,N',N'-tetramethyluronium hexafluorophosphate) (HATU) and 2% by weight of N,N-Diisopropylethylamine (DIEA) dissolved in NMP. In some embodiments, the activating formulation comprises 4% by weight of Benzotriazol-1-yl-oxytripyrrolidinophosphonium hexafluorophosphate (PyBOP) and 2% by weight of DIEA dissolved in NMP.

In some embodiments, the solvent is water. In some embodiments, the solvent is about 80-90% by weight of the total formulation concentration. In some embodiments, the solvent is about 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% by weight of the total formulation concentration. In preferred embodiments, a polymer is about 0.5-5% by weight of the total formulation concentration.

In some embodiments, a coupling reagent is a carbodiimide. In some embodiments, a coupling reagent is a triazole. In some embodiments, a coupling reagent is 1-ethyl-3-(3-dimethylaminopropyl) carbodiimide. In some embodiments, a coupling reagent is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% by weight of the total formulation concentration. In preferred embodiments, a coupling reagent is about 0.5-5% by weight of the total formulation concentration.

Linker Formulations

Also disclosed herein is a linker formulation. A linker formulation can include components such as a solvent, a polymer, a linker molecule, and a coupling reagent. In some embodiments, the polymer comprises 1% by weight polyvinyl alcohol and 2.5% by weight poly vinyl pyrollidone, the linker molecule is 1.25% by weight polyethylene oxide, the coupling reagent is 1% by weight 1-ethyl-3-(3-dimethylaminopropyl) carbodiimide, and the solvent includes water. In some embodiments, the polymer is 0.5-5% by weight polyvinyl alcohol and 0.5-5% by weight poly vinyl pyrollidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some embodiments, the solvent is water, an organic solvent, or a combination thereof. In some embodiments, the organic solvent is N methyl pyrrolidone, dimethyl formamide, dichloromethane, dimethyl sulfoxide, or a combination thereof. In some embodiments, the solvent is about 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration. In preferred embodiments, the solvent is about 80-90% by weight of the total formulation concentration.

In some embodiments, the polymer is a polyvinyl pyrrolidone and/or a polyvinyl alcohol. The general structure of polyvinyl alcohol is as follows, where n is any positive integer greater than 1:

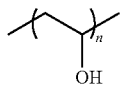

In some embodiments, a polymer is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% by weight of the total formulation concentration. In preferred embodiments, the polymer is about 0.5-5% by weight of the total formulation concentration.

A linker molecule can be a molecule inserted between a surface disclosed herein and a polynucleotide chain that is being synthesized via a coupling molecule. A linker molecule does not necessarily convey functionality to the resulting polynucleotide chain, such as molecular recognition functionality, but can instead elongate the distance between the surface and the polynucleotide chain to enhance the exposure of the polynucleotide chain's functionality region(s) on the surface. In some embodiments, a linker can be about 4 to about 40 atoms long to provide exposure. The linker molecules can be, for example, aryl acetylene, ethylene glycol oligomers containing 2-10 monomer units (PEGs), diamines, diacids, amino acids, and combinations thereof. Examples of diamines include ethylene diamine and diamino propane. Alternatively, linkers can be the same molecule type as that being synthesized (e.g., nascent polymers or various coupling molecules), such as polypeptides and polymers of amino acid derivatives such as for example, amino hexanoic acids, or nucleic acid polymers. In some embodiments, the linker molecule is a molecule having a carboxylic group at a first end of the molecule and a protecting group at a second end of the molecule. In some embodiments, the protecting group is a t-butoxycarbonyl (t-Boc) protecting group or an 9-fluorenylmethoxycarbonyl (Fmoc) protecting group. In some embodiments, the linker molecule is or includes an aryl acetylene, a polyethyleneglycol, a nascent polypeptide, a diamine, a diacid, a peptide, a nucleic acid monomer or polymer, or combinations thereof. In some embodiments, the linker molecule is about less than 0.1, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% by weight of the total formulation concentration. In preferred embodiments, the linker molecule is about 0.5-5% by weight of the total formulation concentration.

The unbound (or free end) portion of the linker molecule can have a reactive functional group which is blocked, protected, or otherwise made unavailable for reaction by a removable protecting group. The protecting group can be bound to the linker molecule to protect a reactive functionality on the linker molecule. Protecting groups that can be used include all acid- and base-labile protecting groups. For example, linker amine groups can be protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that can be used include acid-labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio) carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid-labile groups for protecting carboxylic acids: tert-butyl ester; acid labile groups for protecting hydroxyl groups: dimethyltrityl. See also, Greene, T. W., Protective Groups in Organic Synthesis, Wiley-Interscience, NY, (1981).

Substrates

Also disclosed herein are substrates. In some embodiments, a substrate surface is planar (i.e., 2-dimensional). In some embodiments, a substrate surface is functionalized with free amine groups.

In some aspects, a surface is a material or group of materials having rigidity or semi-rigidity. In some aspects, a surface can be substantially flat, although in some aspects it can be desirable to physically separate synthesis regions for different molecules or features with, for example, wells, raised regions, pins, pillars, etched trenches, or the like. In certain aspects, a surface may be porous. Surface materials can include, for example, silicon, bio-compatible polymers such as, for example poly(methyl methacrylate) (PMMA) and polydimethylsiloxane (PDMS), glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a surface may optionally be coated with one or more layers to provide a second surface for molecular attachment or functionalization, increased or decreased reactivity, binding detection, or other specialized application. Surface materials and or layer(s) can be porous or non-porous. For example, a surface can be comprised of porous silicon. Additionally, the surface can be a silicon wafer or chip such as those used in the semiconductor device fabrication industry. In the case of a wafer or chip, a plurality of arrays can be synthesized on the wafer.

In some embodiments, a substrate includes a porous layer (i.e., a 3-dimensional layer) comprising functional groups for binding a first monomer building block. In some embodiments, a substrate surface comprises pillars for polynucleotide attachment or synthesis. In some embodiments, a porous layer is added to the top of the pillars.

Porous Layer Substrates

Porous layers that can be used may be flat, permeable, polymeric materials of porous structure that have an amine group (that is native to the constituent polymer or that is introduced to the porous layer) for attachment of the first polynucleotide building block. For example, a porous layer can be comprised of porous silicon with functional groups for attachment of a polymer building block attached to the surface of the porous silicon. In another example, a porous layer can comprise a cross-linked polymeric material. In some embodiments, the porous layer can employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly (aspartic acid), poly(ethylene glycol), poly(ethylene oxide), poly(vinyl pyrrolidone), poly(acrylic acid), poly(acrylic acid)-sodium salt, poly(acrylamide), poly(N-isopropyl acrylamide), poly(hydroxyethyl acrylate), poly(acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In some embodiments, the thickness of the porous layer ranges from about 0.01 μm to about 1,000 μm. In preferred embodiments, the thickness of the porous layer ranges from about 0.1 μm to about 500 μm. Pore sizes included in the porous layer may range from 2 nm to about 100 μm. In preferred embodiments, pore sizes may be about 10 nm to about 50 μm.

According to another embodiment of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In some embodiments, the reactive group is a free amine group. The free amine group is free to bind, for example, an activated carboxylic group of a coupling molecule or substituted acetic acid molecule.

In an embodiment, the porous layer is in contact with a support layer. The support layer comprises, for example, metal, plastic, silicon, silicon oxide, or silicon nitride. In another embodiment, the porous layer can be in contact with a patterned surface, such as on top of pillar substrates described below.

Pillar Substrates

In some embodiments, a substrate can include a planar layer having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about $10,000/cm^2$.

In some embodiments, the planar layer comprises metal, plastic, silicon, silicon oxide, or silicon nitride. In some embodiments, the metal is chromium. In some embodiments, the metal is chromium, titanium, aluminum, tungsten, gold, silver, tin, lead, thallium, indium, or a combination thereof. In some embodiments, the planar layer is at least 98.5-99% (by weight) metal, plastic, silicon, silicon oxide, or silicon nitride. In some embodiments, the planar layer is 100% metal, silicon, silicon oxide, or silicon nitride. In some embodiments, the planar layer is at least about 90, 91, 92, 93, 94, 95, 96, 97, 98, 98.5, or 99% metal, silicon, silicon oxide, or silicon nitride. In some embodiments, the layer is a homogenous layer of metal, silicon, silicon oxide, or silicon nitride.

In some embodiments, the distance between the surface of each pillar and the upper surface of the planar layer can be between about less than 1,000, 2,000, 3,000, 3,500, 4,500, 5,000, 5500, 6000, 6500, 7000, 7500, 8000, 8500, 9000, 9500, or 10000 or angstroms (or any integer in between). In particular embodiments, the distance between the surface of each pillar and the upper surface of the planar layer can be about less than 1000-5000 angstroms.

In some embodiments, the surface of each pillar is parallel to the upper surface of the layer. In some embodiments, the surface of each pillar is substantially parallel to the upper surface of the layer.

In some embodiments, the plurality of pillars are present at a density of greater than 500, 1,000, 2,000, 3,000, 4,000, 5,000, 6,000, 7,000, 8,000, 9,000, 10,000, 11,000, or 12,000/$cm^2$ (or any integer in between). In some embodiments, the plurality of pillars are present at a density of greater than $10,000/cm^2$. In some embodiments, the plurality of pillars are present at a density of about $10,000/cm^2$ to about 25 million/$cm^2$ (or any integer in between). In some embodiments, the plurality of pillars are present at a density of greater than 2.5 million/$cm^2$.

In some embodiments, the surface area of each pillar surface is at least 1 $μm^2$. In some embodiments, the surface area of each pillar surface can be at least 0.1, 0.5, 12, 3, 4, 5, 6, 7, 8, 9, 10, 15, 20, 25, 30, 35, 40, 45, or 50 µm² (or any integer in between). In some embodiments, the surface area of each pillar surface has a total area of less than 10,000 µm². In some embodiments, the surface area of each pillar surface has a total area of less than 500, 1,000, 2,000, 3,000, 4,000, 5,000, 6,000, 7,000, 8,000, 9,000, 10,000, 11,000, or 12,000 µm² (or any integer in between).

In some embodiments, the distance between the surface of each pillar and the lower surface of the layer is 2,000-7,000 angstroms. In some embodiments, the distance between the surface of each pillar and the lower surface of the layer is about less than 500, 1,000, 2,000, 3,000, 4,000, 5,000, 6,000, 7,000, 8,000, 9,000, 10,000, 11,000, or 12,000 angstroms (or any integer in between). In some embodiments, the distance between the surface of each pillar and the lower surface of the layer is 7,000, 3,000, 4,000, 5,000, 6,000, or 7,000 angstroms (or any integer in between).

In some embodiments, the layer is 1,000-2,000 angstroms thick. In some embodiments, the layer is about less than 500, 1,000, 2,000, 3,000, 4,000, 5,000, 6,000, 7,000, 8,000, 9,000, 10,000, 11,000, or 12,000 angstroms thick (or any integer in between).

In some embodiments, the center of each pillar is at least 2,000 angstroms from the center of any other pillar. In some embodiments, the center of each pillar is at least about 500, 1,000, 2,000, 3,000, or 4,000 angstroms (or any integer in between) from the center of any other pillar. In some embodiments, the center of each pillar is at least about 2 µm to 200 µm from the center of any other pillar.

In some embodiments, at least one or each pillar comprises silicon. In some embodiments, at least one or each pillar comprises silicon dioxide or silicon nitride. In some embodiments, at least one or each pillar is at least 90, 91, 92, 93, 94, 95, 96, 97, 98, 98.5, or 99% (by weight) silicon dioxide.

In some embodiments, a substrate includes a linker molecule having a free amino terminus attached to the surface of each pillar. In some embodiments, a substrate includes a linker molecule having a free amino terminus attached to the surface of at least one pillar. In some embodiments, a substrate includes a linker molecule having a protecting group attached to the surface of each pillar. In some embodiments, a substrate includes a linker molecule having a protecting group attached to the surface of at least one pillar. In some embodiments, a substrate includes a coupling molecule attached to the surface of at least one pillar. In some embodiments, a substrate includes a coupling molecule attached to the surface of each pillar. In some embodiments, a substrate includes a polymer in contact with the surface of at least one of the pillars. In some embodiments, a substrate includes a polymer in contact with the surface of each pillar. In some embodiments, a substrate includes a gelatinous form of a polymer in contact with the surface of at least one of the pillars. In some embodiments, a substrate includes a solid form of a polymer in contact with the surface of at least one of the pillars.

In some embodiments, the surface of at least one of the pillars of the substrate is derivatized. In some embodiments, a substrate includes a polymer chain attached to the surface of at least one of the pillars. In some embodiments, the polymer chain comprises a polynucleotide chain. In some embodiments, the attachment to the surface of the at least one pillar is via a covalent bond.

In some embodiments, the surface of each pillar is square or rectangular in shape. In some embodiments, the substrate can be coupled to a silicon dioxide layer. The silicon dioxide layer can be about 0.5 µm to 3 µm thick. In some embodiments, the substrate can be coupled to a wafer, e.g., a silicon wafer. The silicon dioxide layer can be about 700 µm to 750 µm thick.

Arrays

Also disclosed herein are arrays. In some embodiments, an array is a two-dimensional array. In some embodiments, the array comprises a surface comprising a substrate and the substrate comprising: a planar layer having an upper surface and a lower surface.

In some embodiments, a two-dimensional array includes features attached to a surface at positionally-defined locations, said features each comprising: a collection of polynucleotide chains of determinable sequence and intended length, wherein within an individual feature, the fraction of polynucleotides within said collection having the intended length is characterized by an average coupling efficiency for each coupling step of about 98%. In some embodiments, the array comprises a plurality of pillars operatively coupled to the layer in the positionally-defined locations, wherein each pillar has a planar surface extended from the layer, wherein the distance between the surface of each pillar and the upper surface of the layer is between 1,000-5,000 angstroms, and wherein the plurality of pillars are present at a density of greater than 10,000/cm².

In some embodiments, the surface of the array is functionalized with free amine groups. In some embodiments, the surface density of free amine groups on the array is greater than 10/cm², 100/cm², 1,000/cm², 10,000/cm², 100,000/cm², 1,000,000/cm², or 10,000,000/cm². In some embodiments, the surface density of the features on the array is greater than 10/cm², 100/cm², 1,000/cm², 10,000/cm², 100,000/cm², 1,000,000/cm², or 10,000,000/cm².

In some embodiments, an array is a three-dimensional array, e.g., a porous array comprising features attached to the surface of the porous array. In some embodiments, the surface of a porous array includes external surfaces and surfaces defining pore volume within the porous array. In some embodiments, a three-dimensional array includes features attached to a surface at positionally-defined locations, said features each comprising: a collection of polynucleotide chains of determinable sequence and intended length. In one embodiment, within an individual feature, the fraction of polynucleotide chains within said collection having the intended length is characterized by an average coupling efficiency for each coupling step of greater than 98%.

In some embodiments, the average coupling efficiency for each coupling step for binding of an incoming nucleotide to a terminal nucleotide during polynucleotide synthesis is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, the purity of each feature with regards to the fraction of full-length predetermined polynucleotide chains is a fraction F of the full-length predetermined polynucleotide chains of each feature having a predetermined sequence and a predetermined full-length sequence length $N$ being characterized by $F=10^{(N+1)-log(E/100\%)}$. In some embodiments, F is characterized by an average coupling efficiency E of at least 98.5% for coupling each monomer of the predetermined sequence. In some embodiments, F is characterized by an average coupling efficiency E of at least 98.5% for coupling each monomer of the predetermined sequence. In some embodiments, the average coupling efficiency E for each coupling step is 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, the distribution of sequence lengths on the array based on the synthesis of a polynucleotide sequence of a defined length (e.g., a 64 mer). At each coupling step, the length of a sequence where a desired coupling does not occur becomes fixed at that length when a capping solution is used. The distribution of lengths according to the step yield for each sequence length less than the full sequence is given by the following equation:

$$F(N) = 10^{(N+1)-log(E/100\%)} - 10^{(N)-log(E/100\%)}$$

where F(N) is the proportion of sequences on the array at a length N that are less than the full length sequence, and where E is the average coupling efficiency percentage. The precise value of E at each length N can also be used to generate an exact number of oligomers at each length.

The proportion of full length sequence may be given by the following equation:

$$F(N) = 10^{(N)-log(E/100\%)}$$

where F(N) is the proportion of sequences on the array of a full length sequence (no further coupling steps), and where E is the average coupling efficiency.

In some embodiments, the sequence length N is at least 64 monomers in length and the fraction of the less than full-length predetermined polynucleotide chains equaling (1−F). In some embodiments, the sequence length N is at least 65 monomers in length.

In some embodiments, each polynucleotide chain is from 5 to 100 monomers in length. In some embodiments, each polynucleotide chain is at least 64 monomers in length. In some embodiments, each polynucleotide chain is at least 65 monomers in length. In some embodiments, each polynucleotide chain is at least 100 monomers or greater than 100 monomers in length. In some embodiments, each polynucleotide chain is at least 5, 10, 15, 20, 25, 30, 35, 40, 45, 50, 55, 60, 65, 70, 75, 80, 85, 90, 95, or 100 monomers in length. In some embodiments, each polynucleotide chain is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or greater than 100 monomers in length. In some embodiments, each polynucleotide chain comprises one or more modified nucleotides. In some embodiments, each polynucleotide comprises one or more ribonucleotides.

An array can include at least 1,000 different features attached to the surface. An array can include at least 10,000 different features attached to the surface. An array can include at least 100, 500, 1000, 2000, 3000, 4000, 5000, 6000, 7000, 8000, 9000, 10,000, or greater than 10,000 different features attached to the surface (or any integer in between).

In some embodiments, an array includes at least 1,000 different polynucleotide chains attached to the surface. In some embodiments, an array includes at least 10,000 different polynucleotide chains attached to the surface. In some embodiments, an array includes at least 100, 500, 1000, 2000, 3000, 4000, 5000, 6000, 7000, 8000, 9000, 10,000, or greater than 10,000 different polynucleotide chains attached to the surface (or any integer in between).

In some embodiments, each feature comprises at least 500 identical full-length polynucleotide chains, wherein each identical polynucleotide chain has a predetermined full-length of at least 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 monomers in length. In some embodiments, each feature comprises 100, 200, 300, 400, 500, 600, 700, 800, 900, 1000, 1100, 1200, 1300, 1400, 1500, 1600, 1700, 1800, 1900, or 2000 identical polynucleotide chains, wherein each identical polynucleotide chain has a predetermined full-length of at least 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or greater than 100 monomers in length.

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, each feature is attached to a surface of the array at a different positionally-defined location and the positionally-defined location of each feature corresponds to a positionally-defined location of a pillar, wherein the top surface of each pillar is at least 1 $\mu m^2$ in size.

In some embodiments, the features are covalently attached to the surface. In some embodiments, said polynucleotide chains are attached to the surface through a linker molecule or a coupling molecule.

In some embodiments, the features comprise a plurality of distinct, nested, overlapping polynucleotide chains comprising subsequences derived from a source DNA or RNA sequence having a known sequence. In some embodiments, each polynucleoside chain in the plurality is substantially the same length. In some embodiments, each polynucleotide chain in the plurality is the same length.

In some embodiments, each polynucleotide chain in a feature is substantially the same length. In some embodiments, each polynucleotide chain in a feature is the same length. In some embodiments, the features comprise a plurality of polynucleotide chains each having a random, determinable sequence of monomers.

Methods

Methods of Manufacturing Substrates

Also disclosed herein are methods for making substrates. In some embodiments, a method of producing a substrate includes coupling a porous layer to a support layer. The support layer can comprise any metal or plastic or silicon or silicon oxide or silicon nitride. In one embodiment, the substrate comprises multiple amino groups attached to the substrate for binding nucleic acid monomers during polynucleotide synthesis. In some embodiments, a method of producing a substrate includes coupling a porous layer to a plurality of pillars, wherein the porous layer comprises functional groups for attachment of a compound to the substrate, wherein the plurality of pillars are coupled to a planar layer in positionally-defined locations, wherein each pillar has a planar surface extended from the planar layer, wherein the distance between the surface of each pillar and the upper surface of the planar layer is between about 1,000-5,000 angstroms, and wherein the plurality of pillars are present at a density of greater than about 10,000/cm$^2$.

In some embodiments, the surface of each pillar is parallel to the upper surface of the planar layer. In some embodiments, the surface of each pillar is substantially parallel to the upper surface of the planar layer.

Surface Derivatization

Substrates can be surface derivatized in a semiconductor module as explained in U.S. Patent Publication No. 2010/0240555, herein incorporated by reference, in its entirety, for all purposes. An exemplary substrate comprise pillars of oxide ready to be surface derivatized. Surface derivatization is a method wherein an amino silane group is added to the substrate so that free amino groups are available for coupling the biomolecules. In some aspects, the first molecule to be attached to the surface derivatized substrate is a t-Boc protected Glycine. This coupling procedure is similar to a standard Merrifield solid phase peptide synthesis procedure, which is generally known to one skilled in this art.

In some embodiments, a method of preparing a substrate surface includes obtaining a surface comprising silicon dioxide and contacting the surface with a photoresist formulation comprising a photoactive compound and a photoprotective compound, optionally including a polymer and a solvent; and applying ultraviolet light to positionally-defined locations located on the top of the surface and in contact with the photoresist formulation. In some aspects, the method can include removing the photoresist formulation located external to the positionally-defined locations.

Methods of Manufacturing Arrays

Also disclosed herein are methods for manufacturing arrays. In some embodiments, the arrays disclosed herein are synthesized in situ on a surface, e.g., a substrate disclosed herein. In some instances, the arrays are made using photolithography. In an exemplary embodiment, the substrate is contacted with a photoresist formulation. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the free amine group. The process can be repeated to synthesize a large number of features in specific or positionally-defined locations on a surface (see, for example, U.S. Pat. No. 5,143,854 to Pirrung et al., U.S. Patent Publication Nos. 2007/0154946, 2007/0122841, 2007/0122842, 2008/0108149, and 2010/0093554, each of which is herein incorporated by reference).

In some embodiments, the features are attached to the surface using a photoresist formulation, comprising a photoactive compound, a photo-protective compound, and optionally: a polymer, and a solvent. In some embodiments, the features are attached to the surface using a photoresist formulation disclosed herein. In some embodiments, the photoresist formulation is stripped away using water.

Also described herein are processes of manufacturing an array. In an exemplary embodiment, a surface comprising attached free amine groups or protected terminal nucleotides is provided. The surface is contacted with a photoresist formulation comprising a photoactive compound, a photoprotective compound, and optionally: a polymer, and a solvent. The surface is exposed to electromagnetic radiation, for example, ultraviolet (UV) light in a deep ultra violet scanner tool according to a pattern defined by a photomask, wherein the locations exposed to radiation undergo photoacid generation due to the presence of a photoacid generator in the photoresist formulation. In some embodiments, the expose energy is about 1 mJ/cm$^2$ to about 5 J/cm$^2$. In preferred embodiments, the expose energy is about 1 mJ/cm$^2$ to about 100 mJ/cm$^2$. In some embodiments, the radiation includes UV light at 248 nm. In some embodiments, the radiation includes 365 nm ultraviolet light. Radiation to activate a photoacid generator can be in a range of wavelengths, and is not limited to wavelengths disclosed herein.

The surface may be post baked upon exposure in a post exposure bake module. Post exposure bake may act as a chemical amplification step. The baking step may amplify the initially generated photoacid and also enhances the rate of diffusion to the substrate. The post bake temperature can vary between 75° Celsius to 115° Celsius, depending on the thickness of the porous surface or the planar layer of the substrate. The surface may be post baked for about 60 seconds to about 120 seconds.

The photoresist formulation may then be stripped away. Described herein is a method of stripping the photoresist completely with deionized (DI) water. In some embodiments, the process is accomplished in a developer module. In one embodiment, the wafer is spun on a vacuum chuck for, e.g., 60 seconds to 90 seconds and deionized water is dispensed through a nozzle for about 30 seconds.

The photoresist formulation can be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. In some embodiments, the substrate is spun on a vacuum chuck for about 10 seconds to about ten minutes. In some embodiments, the substrate is spun for about 10 seconds to about 3 minutes. In some embodiments, the substrate is spun at about 500 rpm to about 10,000 rpm. The substrate may be spun on a vacuum chuck for 15-30 seconds and the photoactive coupling formulation may be dispensed. The spin speed can be set to 2000 to 2500 rpm. In some cases, the substrate is spun at about 2000-2500 rpm for about 15-30 seconds. In some cases, the substrate is spun at about 500 rpm for about 180 seconds. In some cases, the substrate is spun at about 10,000 rpm for about 10 seconds.

Optionally, a cap film solution coat may be applied on the surface to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, dimethyl formamide, or combinations thereof. The capping molecule is typically acetic anhydride and the polymer can be polyvinyl pyrrolidone, polyvinyl alcohol, polymethyl methacrylate, poly (methyl iso propenyl) ketone, or poly (2 methyl pentene 1 sulfone). In some embodiments, the capping molecule is ethanolamine.

This process may utilize a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. In some embodiments, the substrate is spun on a vacuum chuck for about 10 seconds to about ten minutes. In some embodiments, the substrate is spun for about 10 seconds to about 3 minutes. In some embodiments, the substrate is spun at about 500 rpm to about 10,000 rpm. The substrate may be spun on a vacuum chuck for 15-30 s and the coupling formulation may be dispensed. The spin speed can be set to 2000 to 2500 rpm. In some cases, the substrate is spun at about 2000-2500 rpm for about 15-30 seconds. In some cases, the substrate is spun at about 500 rpm for about 180 seconds. In some cases, the substrate is spun at about 10,000 rpm for about 10 seconds.

The substrates with the capping solution may be baked in a cap bake module. A capping bake module can be a hot plate set up specifically to receive wafers just after the capping film coat is applied. In some embodiments, provided herein is a method of baking the spin coated capping coat solution in a hot plate to accelerate the capping reaction significantly. Hot plate baking can reduce the capping time to less than two minutes.

In an embodiment, the byproducts of the capping reaction are stripped in a stripper module. A stripper module can include several nozzles, typically up to 10, set up to dispense organic solvents such as acetone, iso propyl alcohol, N methyl pyrrolidone, dimethyl formamide, DI water, etc. In some embodiments, the nozzles are designated for acetone followed by iso propyl alcohol to be dispensed onto the spinning wafer. The spin speed may be set to be 2000 to 2500 rpm for around 20 seconds.

This entire cycle can be repeated as desired with different coupling molecules each time to obtain a polynucleotide chain of determinable sequence and intended length.

Methods of Use of Polynucleotide Microarrays

Also disclosed herein are methods of using substrates, formulations, and/or arrays. Uses of the arrays disclosed herein can include, e.g., research applications, therapeutic purposes, medical diagnostics, and/or stratifying one or more patients.

Any of the arrays described herein can be used as a research tool or in a research application. In one aspect, arrays can be used for high throughput screening assays. For example, polynucleotide arrays can be tested by subjecting the array to a DNA or RNA molecule and identifying the presence or absence of the complimentary DNA, RNA, or PNA molecule, e.g., by detecting at least one change among the features of the array.

In some embodiments, an array is used for detection of sequence variants in a sample, e.g., single nucleotide polymorphisms (SNPs). Detection of sequence variants can occur through observing sequence-specific hybridization of labeled molecules to a probe on an array. Detection of sequence variants can also occur through binding of a sequence suspected of having a sequence variant to a probe on an array, followed by performing a polymerase extension reaction with a labelled nucleotides. In preferred embodiments, polynucleotide probes are synthesized on the array and hybridize to nucleotide sequences from a sample suspected of comprising a sequence variant. The polynucleotides can be enzymatically active, i.e., they are capable of acting as a substrate for complementary nucleotide incorporation into a growing strand using a polymerase under preferred conditions for polymerization.

Arrays can also be used in screening assays for ligand binding, to determine substrate specificity, or for the identification of complimentary polynucleotide molecule that is expressed in certain cells in vivo or in vitro. Such screening assays can employ, e.g., labeling techniques, protease assays, or binding assays as may be known to those of skill in the art.

In some embodiments, an array is used to represent a predefined polynucleotide sequence using overlapping polynucleotide sequences. For example, the polynucleotide sequence of a known gene is divided into overlapping sequence segments of any length and of any suitable overlapping frame, and polynucleotide chains corresponding to the respective sequence segments are in-situ synthesized as disclosed herein.

In some embodiments, a sample is applied to an array having a plurality of random polynucleotide chains. The random polynucleotide chains can be screened and BLASTed to determine homologous domains with, e.g., a 90% or more identity to a given nucleotide sequence. In some aspect, the whole polynucleotide sequence can then be synthesized and used to identify potential markers and/or causes of a disease of interest.

In some embodiments, an array is used for high throughput screening of one or more genetic factors. DNA or RNA expression associated with a gene can be investigated through polynucleoside hybridization, which can then be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, PNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, polynucleotides, chemicals, natural extracts, peptides, proteins, fragments of antibodies, antibody like molecules, or antibodies. In some embodiments, test compounds are hybridizing DNA, RNA or PNA sequences. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In one aspect, also provided are arrays for use in medical diagnostics. An array can be used to determine a response to administration of drugs or vaccines. For example, an individual's response to a vaccine can be determined by detecting the gene expression levels of the individual by using an array with polynucleotide chains representing particular genes associated with the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a expressed gene of interest in a sample includes obtaining an array disclosed herein and contacted with a sample suspected of comprising the DNA or RNA sequence of a gene of interest; and determining whether the gene of interest is expressed in the sample by detecting the presence or absence of binding to one or more features of the array. In some embodiments, the DNA or RNA sequence of the gene of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate includes obtaining an array disclosed herein contacted with a sample derived from a subject previously administered the vaccine candidate, wherein the sample comprises a plurality of DNA or RNA sequences; and determining the binding specificity of the plurality of DNA or RNA sequences to one or more features of the array. In some embodiments, the features comprise a plurality of distinct, nested, overlapping polynucleotide chains comprising subsequences derived from a known nucleotide sequence.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way.

Example 1: Synthesis of a Functionalized Array for Polynucleotide Synthesis

A silicon dioxide wafer functionalized for subsequent polynucleotide synthesis was prepared as follows:

Patterned silicon dioxide wafers were obtained from SVMI. The wafer was then functionalized using (3-Aminopropyl) triethoxysilane (APTES) as follows: APTES was added to Ethanol to final concentration of 2% by weight and the mixture was spin-coated on the wafer. After spin coating, the wafer was baked at 100° C. for 30 minutes.

Next, Fmoc-NH-PEG6-CH2CH2COOH was coupled to APTES bound to the wafer surface. An Fmoc-NH-PEG6-CH2CH2COOH solution was created by dissolving Fmoc-NH-PEG6-CH2CH2COOH in 1-Methyl-2-Pyrrolidinone solvent. 1-Hydroxy-7-azabenzotriazole (HOAt) was added to the solution. The solution was stirred for 15 minutes at room temperature. Diisopropylcarbodiimide (DIC) was added to a 5 mL aliquot of the resulting solution. This solution was heated at 60° C. for 15 minutes.

The final concentration of each reagent in the 1-Methyl-2-Pyrrolidinone solvent was as follows:

Fmoc-NH-PEG6-CH2CH2COOH (0.1M)
HOAt (0.1M)
DIC (0.1M)

This solution was then spin coated on the APTES functionalized wafer to couple Fmoc-NH-PEG6-CH2CH2COOH to APTES on the wafer surface. The wafer was then stripped with a solution of 1-Methyl-2-Pyrrolidinone and Isopropyl alcohol. The resulting wafer was thereby functionalized with Fmoc-protected amine groups at the end of long chains bound to the surface of the wafer.

4-methylpiperidine was added to 1-methyl-2-pyrrolidinone solvent at a concentration of 20% by weight. 5 mL of the mixture was spin coated on the wafer.

To prepare the array for subsequent polynucleotide synthesis, an initial coupling step of a DMT-protected phosphoramidite to the Fmoc-protected NH group was performed. Thymine CED phosphoramidite was dissolved into Acetonitrile solvent and the mixture was stirred at room temperature for 15 minutes. To the mixture 5-benzothio tetrazole was added and then stirred again at room temperature. The final concentration of Thymine CED phosphoramidite was 0.2M and the final concentration of 5-benzothio tetrazole was 0.25M. The mixture was then spin coated on the wafer to couple the DMT-protected phosphoramidite to the NH-PEG6-CH2CH2COOH bound to the array surface. The wafer was then stripped with Acetonitrile and Isopropyl Alcohol.

A solution of 50% of Cap A (Acetic Anhydride/Pyridine/THF) and 50% of Cap B (16% N-Methylimidazole in THF) was mixed together and stirred at room temperature for 5 minutes. Cap A and Cap B solutions were obtained from ChemGenes Corporation. The mixture was then spin coated on the wafer to cap any deprotected amine groups that did not bind to the Thymine CED phosphoramidite. The wafer was then stripped using Acetonitrile and Isopropyl alcohol. Oxidation solution was spin coated on the wafer. Oxidation solution was obtained from ChemGenes Corporation. The wafer was then stripped using Acetonitrile and Isopropyl alcohol.

A fluorescence experiment using 5(6)-FAM was performed to confirm the presence of terminal DMT-protected Thymine CED phosphoramidites. Briefly, the array was incubated with 5(6)-FAM. Because 5(6)-FAM only couples with unprotected thymidine, a low fluorescence signal intensity may indicate successful DMT protection. After uncoupled FAM was washed away, a first signal intensity was measured. After measurement, DMT groups were cleaved using TCA. A linker (MMT-C6 CED-phosphoramidite) was coupled to the thymine residues to convert the OH on the deprotected thymines to NH2. The array was then reincubated with 5(6)-FAM. After uncoupled FAM was washed away, a second signal intensity was measured. In this experiment, the first signal intensity was 134, and the second signal intensity was 65535. This experiment confirmed that the resulting array comprised a plurality of terminal DMT-protected Thymine CED phosphoramidites for subsequent nucleotide synthesis reactions.

Example 2: Polynucleotide Synthesis on a Microarray Using a Photoactivated Acid Cascade System A photoactive solution for generating a photoactivated acid cascade reaction on the array was prepared as follows: PMMA was added in small portions to PGMEA to a final concentration of 2% by weight and the mixture was stirred at room temperature for 48 hours to dissolve the PMMA. To the PGMEA-PMMA solution, 4-tert butyl phenyl acetate was added to a final concentration of 5% by weight and the mixture was stirred at room temperature for 15 minutes. Finally, ITX was added to the resulting solution at a final concentration of 5% by weight and the solution was stirred at room temperature for 15 minutes.

An array comprising a plurality of DMT-protected nucleotides (DMT-R1) was prepared as described in Example 1. The photoactive solution was spin coated on the wafer. The wafer was then exposed in the Nikon NSR i10-365 nm photolithography stepper tool at selected locations using a photomask. The exposure time was 500 ms per field to 365 nm wavelength light. After the exposure was completed, a post exposure delay was performed by allowing the wafer to sit at room temperature for 10 minutes to complete the deprotection reaction. The wafer was then stripped with acetone and isopropyl alcohol.

A solution containing the desired nucleotide for addition to the deprotected nucleotides was prepared by dissolving a DMT-protected nucleotide in acetonitrile along with 5-benzothiotetrazole and stirring for 5 minutes. The final concentration of the DMT-protected nucleotide was 0.1M and the final concentration of 5-benzothiotetrazole was 0.25M. This solution was then spin coated on the wafer to couple the DMT-protected nucleotide with the deprotected nucleotides bound to the wafer. The wafer was then stripped using acetonitrile and isopropyl alcohol.

A capping solution of 50% Cap A and 50% Cap B solution was mixed together at room temperature and spin coated on the wafer to cap any unprotected nucleotides on the surface of the wafer. The wafer was then stripped using acetonitrile and isopropyl alcohol. Oxidation solution was spin coated on the wafer. The wafer was then stripped using Acetonitrile and Isopropyl alcohol.

Deprotection, coupling, and capping steps were repeated for each desired location specific nucleotide synthesis to generate a desired array of sequence-specific synthesized polynucleotides.

Example 3: Two-Step Polynucleotide Synthesis on an Array Using In Situ Synthesized NPPOC Protection In this example, we describe sequence-specific polynucleotide synthesis on an array using an in situ synthesized NPPOC protection group to facilitate site-specific nucleotide addition. The process performed was a two-step reaction, where photoactivated deprotection and nucleotide coupling were performed in separate steps.

An array comprising a plurality of DMT-protected nucleotides (DMT-R1) was prepared as described in Example 1. DMT was globally removed from the DMT-protected nucleotides bound to the wafer by spin coating a solution of trichloroacetic acid (TCA) and dichloromethane on the wafer. The wafer was then stripped using acetonitrile and isopropyl alcohol.

In situ synthesis of NPPOC to each of the deprotected nucleotides bound to the wafer was performed by spin coating a solution comprising 0.3M 2-(2-nitrophenyl) propyl chloroformate dissolved in a solvent of 30% 1-methyl-2-pyrrolidinone and 70% pyridine onto the wafer. The wafer was baked at 95° C. for two minutes to globally couple the NPPOC protecting group to the deprotected nucleotides bound to the wafer. The wafer was then stripped with 1-methyl-2-pyrrolidinone and isopropyl alcohol.

A photoresist solution to facilitate deprotection the NPPOC-protected nucleotides was prepared by adding PMMA at a concentration of 2% by weight to NMP and stirring the solution for 24 hours. To this solution ITX was added to a final concentration of 5% by weight and stirred at room temperature for 1 hour. The photoresist solution was then spin coated onto the wafer.

The wafer was then exposed in the Nikon NSR i10-365 nm photolithography stepper tool at selected locations using a photomask to remove the NPPOC-protecting group from selected nucleotides where addition of a selected incoming nucleotide is desired. The exposure time was 5,000 ms per field to 365 nm wavelength light. After exposure was completed, the wafer was stripped with acetone and IPA.

A solution containing the desired nucleotide for addition to the deprotected nucleotides was prepared by dissolving a DMT-protected nucleotide in acetonitrile along with 5-benzothiotetrazole and stirring for 5 minutes. The final concentration of the DMT-protected nucleotide was 0.1M and the final concentration of 5-benzothiotetrazole was 0.25M. This solution was then spin coated on the wafer to couple the DMT-protected nucleotide with the deprotected nucleotides bound to the wafer. The wafer was then stripped using acetonitrile and isopropyl alcohol.

A capping solution of 50% Cap A and 50% Cap B solution was mixed together at room temperature and spin coated on the wafer to cap any unprotected nucleotides on the surface of the wafer. The wafer was then stripped using acetonitrile and isopropyl alcohol. Oxidation solution was spin coated on the wafer. The wafer was then stripped using Acetonitrile and Isopropyl alcohol.

Deprotection, coupling, and capping steps were repeated for each desired location specific nucleotide synthesis to generate a desired array of sequence-specific synthesized polynucleotides.

Example 4: One-Step Polynucleotide Synthesis on an Array Using In Situ Synthesized NPPOC Protection In this example, we describe sequence-specific polynucleotide synthesis on an array using an in situ synthesized NPPOC protection group to facilitate site-specific nucleotide addition. The process performed was a one-step reaction, where photoactivated deprotection and nucleotide coupling were performed in a single step.

An array comprising a plurality of DMT-protected nucleotides (DMT-R1) was prepared as described in Example 1. DMT was globally removed from the DMT-protected nucleotides bound to the wafer by spin coating a solution of trichloroacetic acid (TCA) and dichloromethane on the wafer. The wafer was then stripped using acetonitrile and isopropyl alcohol.

In situ synthesis of NPPOC to each of the deprotected nucleotides bound to the wafer was performed by spin coating a solution comprising 0.3M 2-(2-nitrophenyl) propyl chloroformate dissolved in a solvent of 30% 1-methyl-2-pyrrolidinone and 70% pyridine onto the wafer. The wafer was baked at 95° C. for two minutes to globally couple the NPPOC protecting group to the deprotected nucleotides bound to the wafer. The wafer was then stripped with 1-methyl-2-pyrrolidinone and isopropyl alcohol.

A photoresist solution was prepared by adding PMMA at a concentration of 2% by weight to NMP and stirring the solution for 24 hours. To this solution ITX was added to a final concentration of 5% by weight and stirred at room temperature for 1 hour.

Next, a DMT-protected nucleotide and 5-benzothiotetrazole were added to the photoresist solution at to a final concentration 0.1M and 0.25M, respectively, to facilitate single step NPPOC deprotection and incoming nucleotide addition. The solution was stirred for 5 minutes at room temperature. The photoresist solution was then spin coated onto the wafer.

The wafer was then exposed in the Nikon NSR i10-365 nm photolithography stepper tool at selected locations using a photomask. The exposure time was 5,000 ms per field to 365 nm wavelength light. After exposure was completed, the wafer was stripped with acetone and IPA.

A capping solution of 50% Cap A and 50% Cap B solution was mixed together at room temperature and spin coated on the wafer to cap any unprotected nucleotides on the surface of the wafer. The wafer was then stripped using acetonitrile and isopropyl alcohol. Oxidation solution was spin coated on the wafer. The wafer was then stripped using Acetonitrile and Isopropyl alcohol.

Deprotection, coupling, and capping steps were repeated for each desired location specific nucleotide synthesis to generate a desired array of sequence-specific synthesized polynucleotides.

Example 5: Testing the Synthesis Efficiency for Each Reaction Scheme

A 15-mer sequence (ACTTCCGCGCTCTTT, SEQ ID NO: 5) was grown on three different wafers, using each of the three reaction schemes from Examples 2-4. As a control, the same 15-mer sequence was grown using substituted 2-nitrobenzyltrichloroacetate, which produces trichloroacetic acid upon photolysis. In the sequence grown, the 8$^{th}$ mer (underlined) was the SNP position.

We obtained four biotin-labeled oligonucleotide probes having largely complementary pair sequences to the 15-mer sequence, but with different polynucleotides in the 8$^{th}$ position. The complementary sequences were:

```
Mismatch sequence
                                          SEQ ID NO: 1
TGAAGGCACGAGAAA Mismatch sequence
                                          SEQ ID NO: 2
TGAAGGCTCGAGAAA Match sequence
                                          SEQ ID NO: 3
TGAAGGCGCGAGAAA Mismatch sequence
                                          SEQ ID NO: 4
TGAAGGCCCGAGAAA
```

To assess synthesis efficiency, a hybridization and biotin-labeling experiment was performed as follows:

Step 1: 1 µM of the biotin-labeled oligonucleotides having the sequences of SEQ1, SEQ2, SEQ3 or SEQ4 was added separately to 4 different wells in a 96 well plate containing 99 µl of PBS solution.

Step 2: A pillar plate containing the silicon chips was placed over the 96 well plate to allow hybridization of the oligonucleotide probes to the 15-mer sequences grown on the chips. Hybridization was carried out for 30 minutes at room temperature.

Step 3: The chips were washed with PBS solution for 2 minutes. The wash step was repeated 3 times.

Step 4: 1 µl of Alexa 488 Streptavidin was dissolved in 500 µl of PBS solution. 100 ul of this solution was added to the 4 wells in the 96 well plate for 30 minutes.

Step 5: The chips were washed with PBS solution for 2 minutes. The wash step was repeated 3 times.

Step 6: The chips were washed with DI water for 2 minutes and dried with nitrogen. The chips were scanned using a Nikon A1R array scanner at 488 nm wavelength to detect hybridization.

Results are depicted in Tables 2-4.

TABLE 2

Type I (Example 2) - Photoacid cascade synthesis:

| | Sequence name: | | | |
|---|---|---|---|---|
| | SEQ ID NO: 1 | SEQ ID NO: 2 | SEQ ID NO: 3 | SEQ ID NO: 4 |
| Signal: | 524 | 601 | 65535 | 567 |

TABLE 3

Type II (Example 3) - In situ NPPOC synthesis and two-step deprotection and coupling

| Sequence name: | SEQ 1 | SEQ 2 | SEQ 3 | SEQ 4 |
|---|---|---|---|---|
| Signal: | 561 | 574 | 65535 | 503 |

TABLE 4

Type III (Example 4) - In situ NPPOC synthesis and one-step deprotection and coupling

| Sequence name: | SEQ 1 | SEQ 2 | SEQ 3 | SEQ 4 |
|---|---|---|---|---|
| Signal: | 517 | 509 | 65535 | 511 |

TABLE 5

| Control sequence using substituted 2-nitrobenzyltrichloroacetate: | | | | |
|---|---|---|---|---|
| Sequence name: | SEQ 1 | SEQ 2 | SEQ 3 | SEQ 4 |
| Signal: | 785 | 814 | 21126 | 1011 |

Type 1: Results from Tables 2 and 5 show that good hybridization efficiency was achieved using Type 1 which produces acetic acid (low pH), as compared to the control photoacid which produced trichloroacetic acid. Without wishing to be bound by theory, Type 1 carries a low risk of depurination (one of the important issues in a photoacid based polynucleotide microarray). Since acetic acid is produced using a cascade mechanism, complete deprotection of the DMT group can be achieved without depurinating the purines in the sequences. A one-mer coupling cycle took 25 minutes. It took 375 minutes to grow the 15-mer.

Type 2: In type 2, a photocleavable protection group (NPPOC) was used, resulting in little to no depurination. The use of ITX enabled complete deprotection of the NPPOC group in 365 nm UV. These experiments demonstrated that in situ synthesis of NPPOC protections facilitates low cost compared to the synthesis of individual NPPOC protected monomers. A one-mer coupling cycle took 22 minutes. It took 330 minutes to grow the 15-mer.

Type 3: Compared to type 1 and 2, type 3 coupling is performed in one step increasing the turnaround time for each step while maintaining the same efficiency of hybridization. A one-mer coupling cycle took 18 minutes. It took 270 minutes to grow the 15-mer.

As observed from the signals from each of the synthesis schemes tested, only the matching complementary sequence hybridized to the sequence grown on the chip. The control condition using the traditional substituted 2-nitrobenzyl-trichloroacetate method revealed a much lower intensity signal of less than half as compared to polynucleotide arrays generated by Types I, II and III reaction schemes. These results suggesting a more than two-fold increase in the efficiency of the three synthesis schemes tested above.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method for synthesizing a polynucleotide having a pre-defined sequence, the method comprising
   providing a support comprising a protected nucleic acid at a first feature;
   contacting said support with a photoresist solution comprising a photoacid generator, wherein the photoacid generator comprises
   4-tert butyl phenyl acetate and PGMEA;
   4-tert butyl phenyl carbonate and a compound selected from the group consisting of: propylene carbonate, methyl phenyl carbonate, and PGMEA;
   4-tert butyl phenyl phosphate and phenyl phosphate;
   4-tert butyl phenyl sulfonate and a compound selected from the group consisting of: phenyl sulfate, 4 methyl phenyl sulfate, dimethyl sulfate, methyl trifluoromethane sulfonate, and methyl fluorosulfonate;
   4-tert butyl phenyl triflate and phenyl trifluoromethane sulfonate; or
   4-tert butyl phenyl benzoate and phenyl benzoate;
   exposing said support to a wavelength of light, wherein said photoacid generator generates a acid via a cascade reaction upon exposure to the wavelength of light, wherein said acid deprotects the nucleic acid at the first feature; and
   binding a protected nucleic acid to said deprotected nucleic acid at said first feature.

2. The method of claim 1, wherein said acid comprises acetic acid, carbonic acid, phosphoric acid, sulfonic acid, triflic acid, or benzoic acid.

3. The method of claim 1, wherein said photoacid generator comprises 4-tert butyl phenyl acetate and PGMEA.

4. The method of claim 1, wherein said photoacid generator comprises 4-tert butyl phenyl carbonate and a compound selected from the group consisting of: propylene carbonate, methyl phenyl carbonate, and PGMEA.

5. The method of claim 1, wherein said photoacid generator comprises 4-tert butyl phenyl phosphate and phenyl phosphate.

6. The method of claim 1, wherein said photoacid generator comprises 4-tert butyl phenyl sulfonate and a compound selected from the group consisting of: phenyl sulfate, 4 methyl phenyl sulfate, dimethyl sulfate, methyl trifluoromethane sulfonate, and methyl fluorosulfonate.

7. The method of claim 1, wherein said photoacid generator comprises 4-tert butyl phenyl triflate and phenyl trifluoromethane sulfonate.

8. The method of claim 1, wherein said photoacid generator comprises 4-tert butyl phenyl benzoate and phenyl benzoate.

9. The method of claim 1, wherein said protected nucleic acid comprises a DMT group.

10. The method of claim 1, wherein said DMT group is bound to said nucleic acid at a 5' carbon.

11. The method of claim 1, wherein said wavelength of light is about 350 nm.

12. The method of claim 1, further comprising repeating said steps to synthesize a polynucleotide of an intended length and sequence.

13. The method of claim 1, wherein said support comprises at least 10, at least 100, at least 1,000 or at least 10,000 features comprising said protected nucleic acid.

* * * * *

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgaaggcacg agaaa                                                        15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgaaggctcg agaaa                                                        15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
tgaaggcgcg agaaa                                                      15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgaaggcccg agaaa                                                      15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acttccgcgc tcttt                                                      15
```